(12) United States Patent
Ha et al.

(10) Patent No.: US 10,259,850 B2
(45) Date of Patent: Apr. 16, 2019

(54) MODIFIED DKK2 PROTEIN, NUCLEIC ACID ENCODING THE SAME, PREPARATION METHOD THEREOF, AND USE THEREOF

(71) Applicant: MEDPACTO INC., Suwon-si, Gyeonggi-do (KR)

(72) Inventors: Il Ho Ha, Gunpo-si (KR); Seok Ho Yoo, Daejeon (KR); Hye Nan Kim, Seosan-si (KR); Yeung Chul Kim, Daejeon (KR); Ju Ry Lim, Daejeon (KR)

(73) Assignee: MEDPACTO INC., Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/548,580

(22) PCT Filed: Feb. 3, 2016

(86) PCT No.: PCT/KR2016/001175
§ 371 (c)(1),
(2) Date: Aug. 3, 2017

(87) PCT Pub. No.: WO2016/126098
PCT Pub. Date: Aug. 11, 2016

(65) Prior Publication Data
US 2018/0016313 A1 Jan. 18, 2018

(30) Foreign Application Priority Data

Feb. 4, 2015 (KR) .......................... 10-2015-0017479

(51) Int. Cl.
*C07K 14/47* (2006.01)
*A61K 38/00* (2006.01)

(52) U.S. Cl.
CPC .............. *C07K 14/47* (2013.01); *A61K 38/00* (2013.01); *C07K 2319/21* (2013.01); *C07K 2319/30* (2013.01)

(58) Field of Classification Search
CPC ................................ C07K 14/47; A61K 38/00
See application file for complete search history.

(56) References Cited

U.S. PATENT DOCUMENTS

| | | | | |
|---|---|---|---|---|
| 6,344,541 B1 * | 2/2002 | Bass | ...................... | C07K 14/47 530/324 |
| 6,812,339 B1 * | 11/2004 | Venter | .................. | C12Q 1/6883 435/6.11 |
| 6,924,355 B2 * | 8/2005 | Baker | ...................... | C07K 14/47 530/350 |
| 6,936,436 B2 * | 8/2005 | Baker | .................. | C07K 14/705 435/320.1 |
| 7,745,391 B2 * | 6/2010 | Mintz | ...................... | G06F 19/24 514/19.3 |
| 8,450,274 B2 | 5/2013 | Kwon et al. | | |
| 9,241,973 B2 | 1/2016 | Suh et al. | | |
| 2007/0128187 A1 * | 6/2007 | Allen | ...................... | C07K 16/18 424/143.1 |
| 2008/0038775 A1 * | 2/2008 | Allen | .................. | C07K 14/4703 435/69.1 |
| 2010/0216140 A1 | 8/2010 | McCarthy | | |
| 2011/0223184 A1 * | 9/2011 | Kwon | ................ | C07K 14/4703 424/178.1 |
| 2011/0244518 A1 * | 10/2011 | Zheng | ................ | C07K 14/4718 435/69.7 |
| 2012/0141481 A1 | 6/2012 | Ernst et al. | | |
| 2012/0252735 A1 * | 10/2012 | Hearing | ................... | A61K 8/64 514/18.6 |

FOREIGN PATENT DOCUMENTS

| | | |
|---|---|---|
| JP | 2009538295 A | 11/2009 |
| KR | 10-2009-0060334 A | 6/2009 |
| KR | 10-1218806 B1 | 1/2013 |
| KR | 10-2013-0122927 A | 11/2013 |
| WO | 2005/095448 A2 | 10/2005 |
| WO | 2009/155055 A2 | 12/2009 |

OTHER PUBLICATIONS

Y. Mazola, et al; Integrating bioinformatics tools to handle glycosylation; PLoS Computational Biology; vol. 7; Issue 12; e1002285; Dec. 29, 2011; 7 pages.
Y. Katoh, et al; Comparative genomics on DKK2 and DKK4 orthologs; Int. Mol. Med.; vol. 16; No. 3; Sep. 2005; 1 page (abstract).
B.K. Brott, et al; Regulation of Wnt/LRP signaling by distinct domains of dickkopf proteins; Molecular and Cellular Biology; vol. 22; No. 17; Sep. 2002; pp. 6100-6110.
International Search Report dated May 11, 2016 for PCT/KR2016/001175.
Written Opinion dated May 11, 2016 for PCT/KR2016/001175.
Functional and structural diversity of the human Dickkopf gene family, Valery E. Krupnik et al., Elsevier, An International Journal on Genes and Genomes, Gene 238 (1999) p. 301-313, Aug. 6, 1999.
Human Dickkopf-1 (huDKK1) protein: Characterization of glycosylation and determination of disulfide linkages in the two cysteine-rich domains, Mitsuru Haniu et al., Protein Science 2011, vol. 20: p. 1802-1813, Jul. 29, 2011.
Lijun Chen et al. "Structural Insight into the Mechanisms of Wnt Signaling Antagonism by Dkk", Journal of Biological Chemistry, vol. 283, No. 34, Jan. 1, 2008 pp. 23364-23370.

(Continued)

*Primary Examiner* — Amber D Steele
(74) *Attorney, Agent, or Firm* — Lucas & Mercanti, LLP

(57) ABSTRACT

Provided are a modified DKK2 polypeptide according to an aspect, a nucleic acid encoding the same, a preparation method thereof, and use thereof. Accordingly, a modified DKK2 protein having an additional glycosyl group or improved binding affinity for a substrate LRP6 may be efficiently prepared, thereby being used for promoting angiogenesis or preventing or treating vascular permeability-related diseases.

20 Claims, 6 Drawing Sheets
Specification includes a Sequence Listing.

(56) References Cited

OTHER PUBLICATIONS

The extended European Search Report, Application No. 16746839.6, May 24, 2018.
Comparative genomics on DKK2 and DKK4 orthologs, Yuriko Katoh et al., Int.J.Mol.Med., 16(3)2005, p. 477-481.
Integrating Bioinformatics Tools to Handle Glycosylation, Yuliet Mazola et al., PLOS Computation Biology, Dec. 2011, vol. 7, No. 12, e1002285.

* cited by examiner

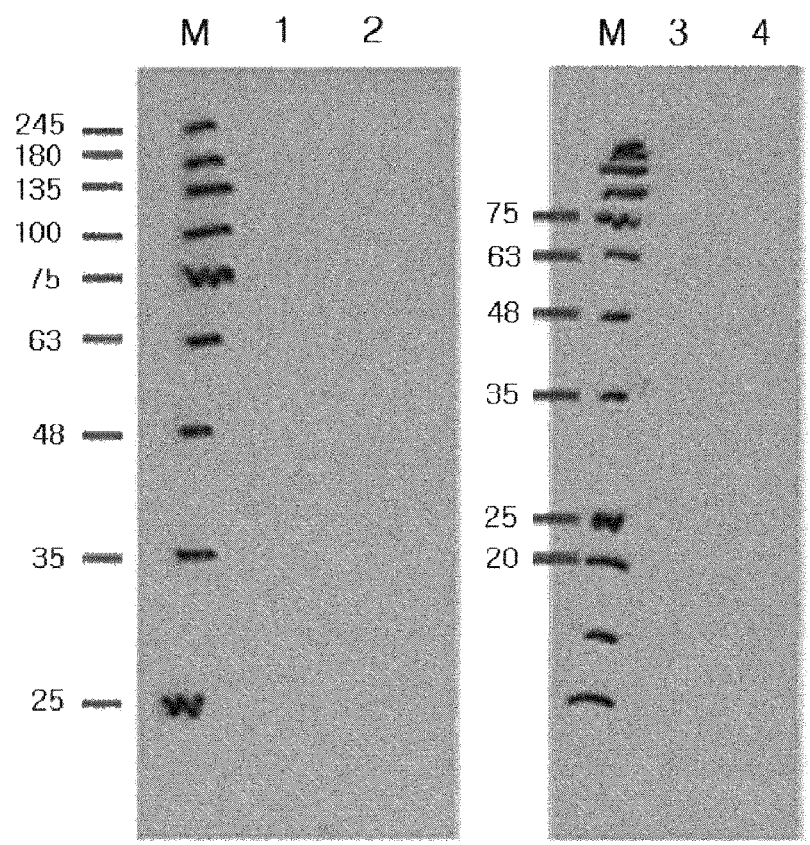
[Fig. 1A]

[Fig. 1B]
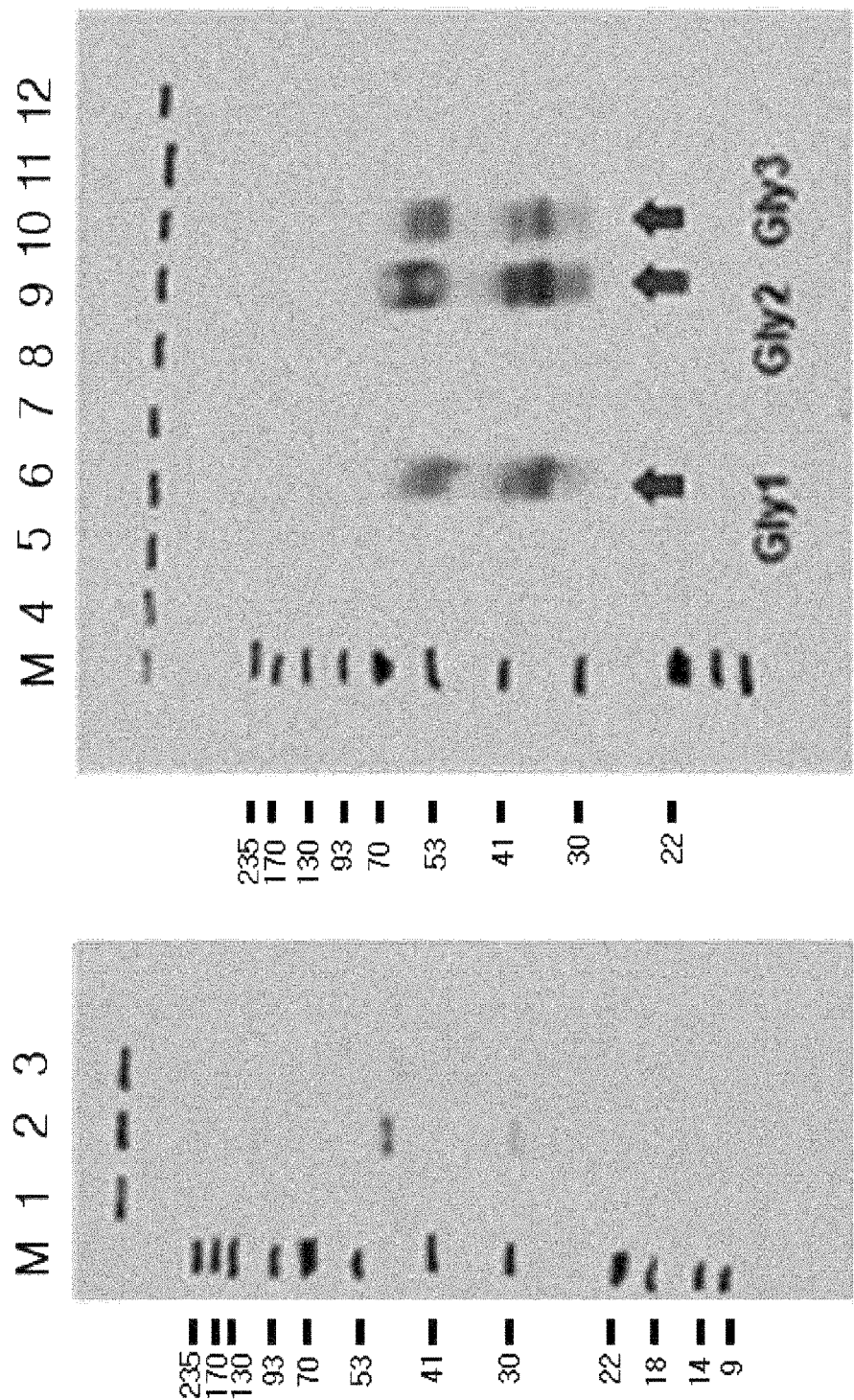

[Fig. 1C]
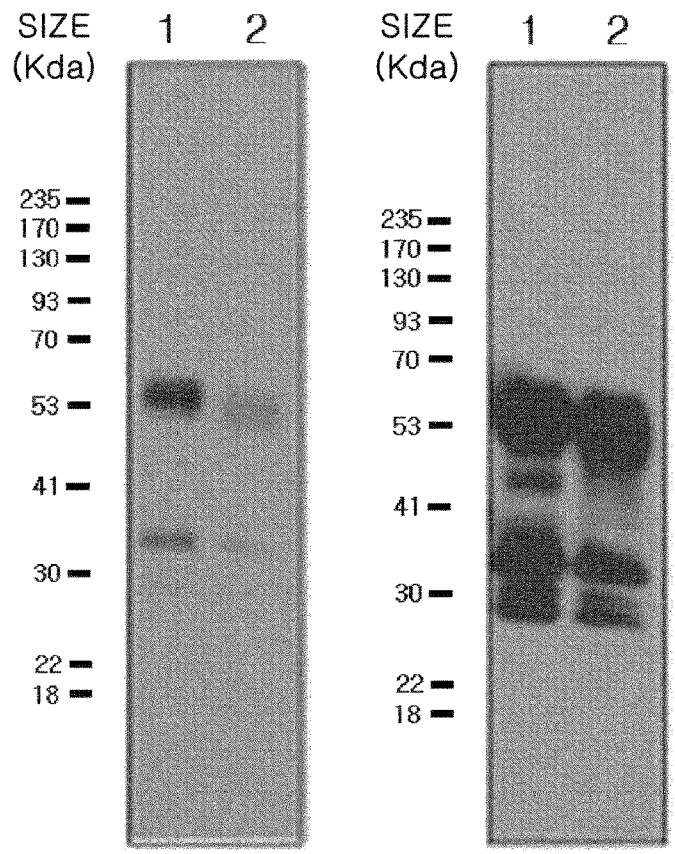
[Fig. 1D]
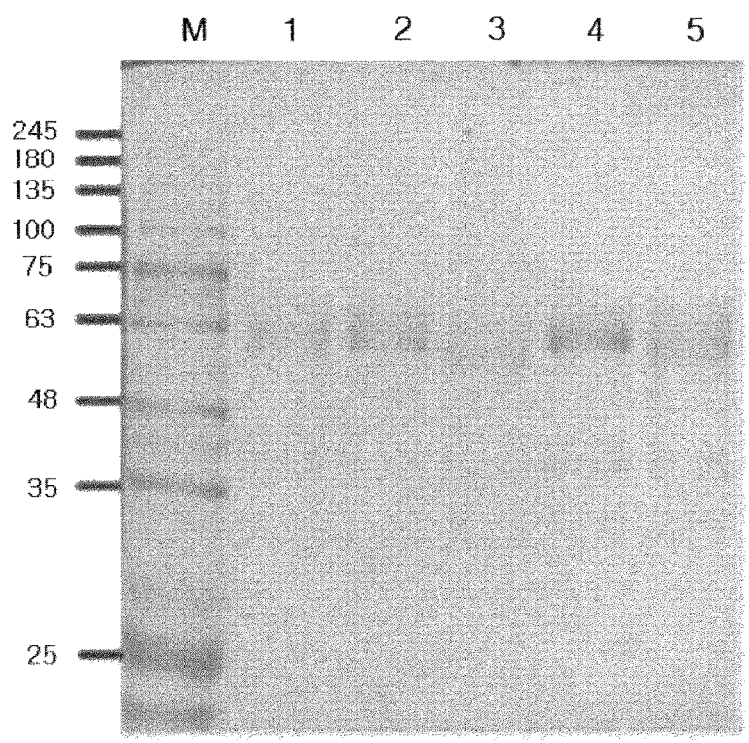

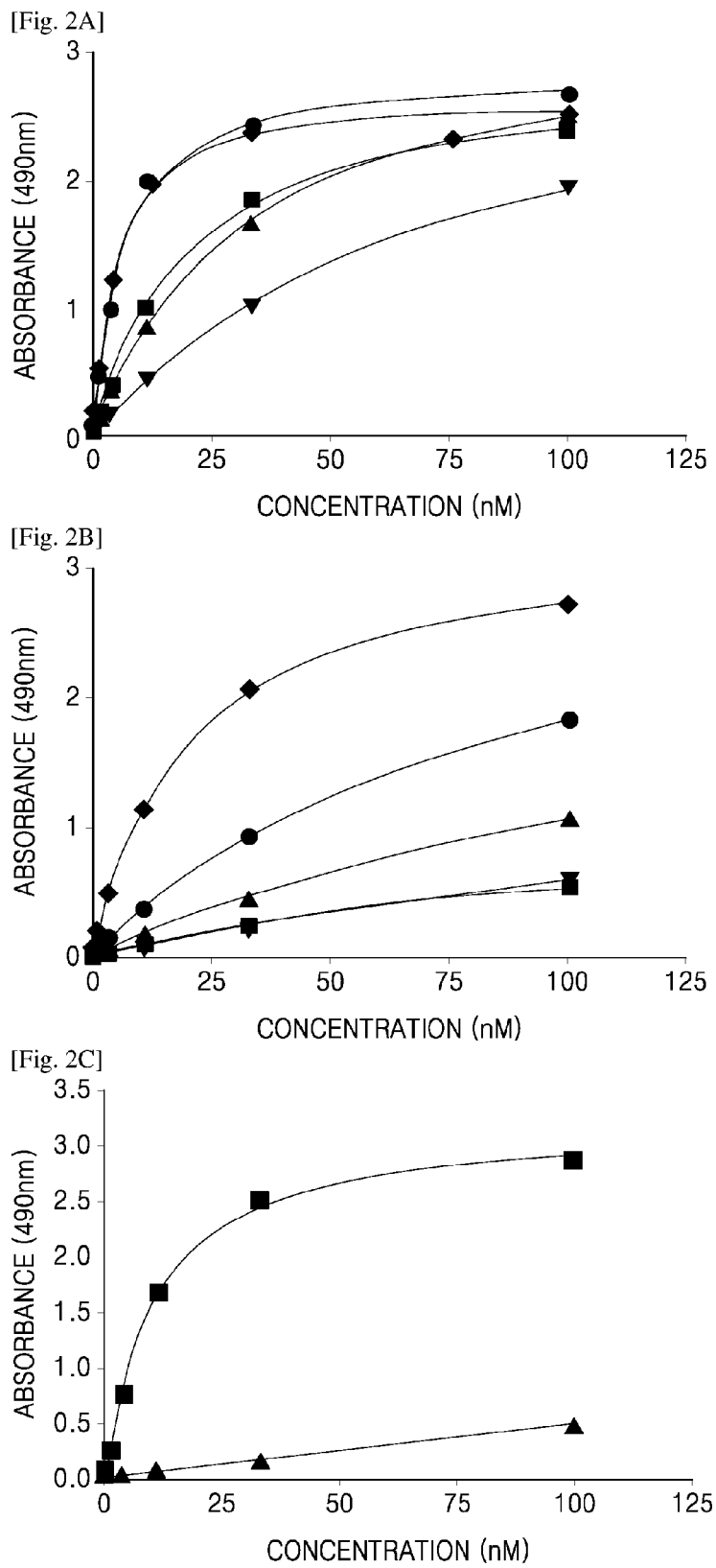

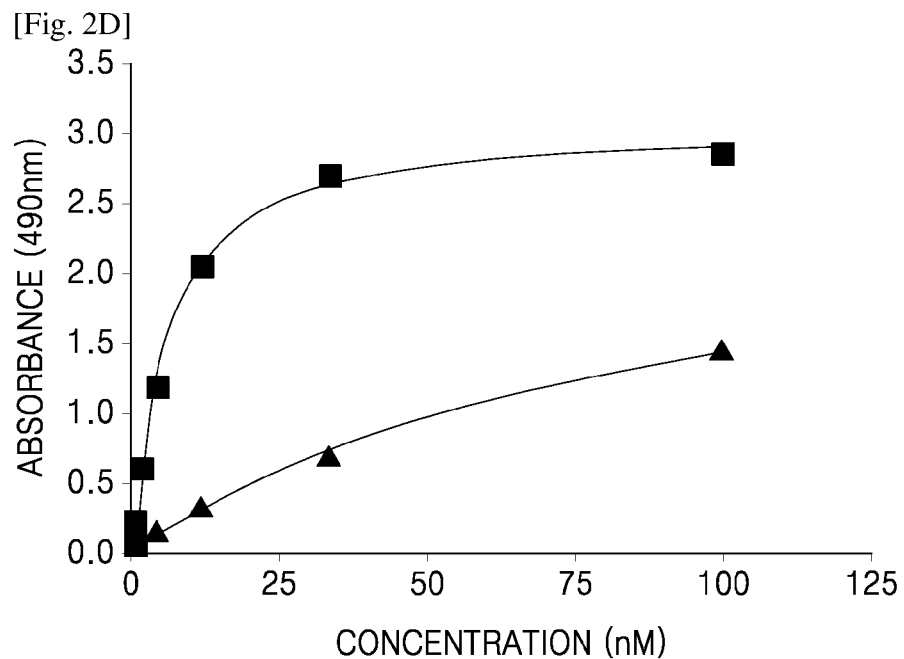
[Fig. 2D]
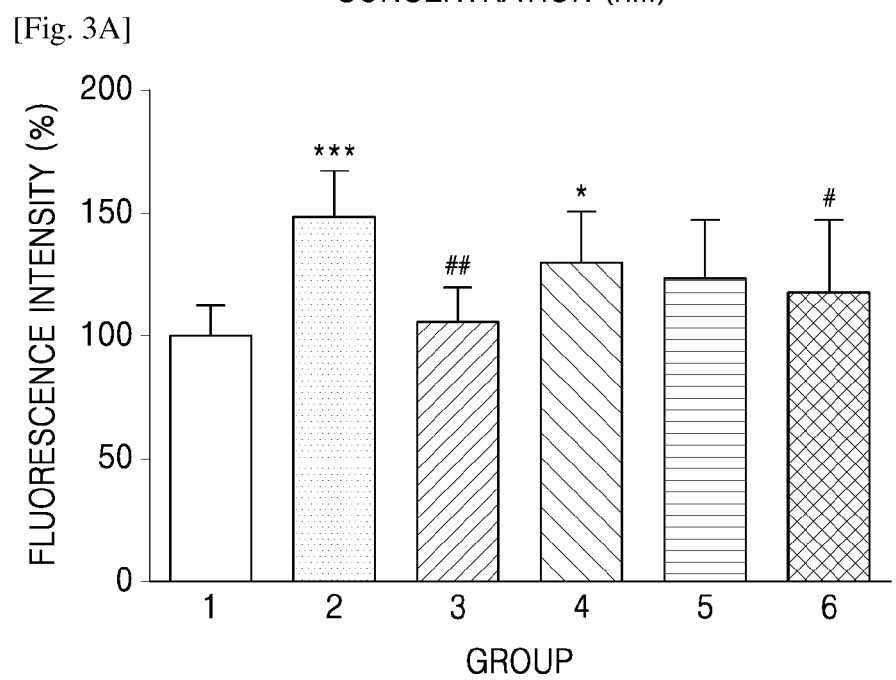
[Fig. 3A]

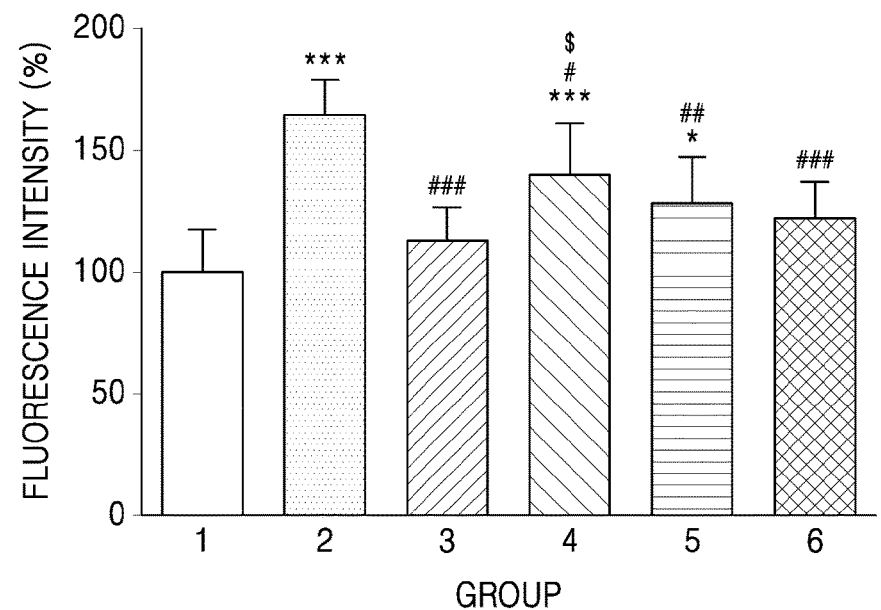
[Fig. 3B]
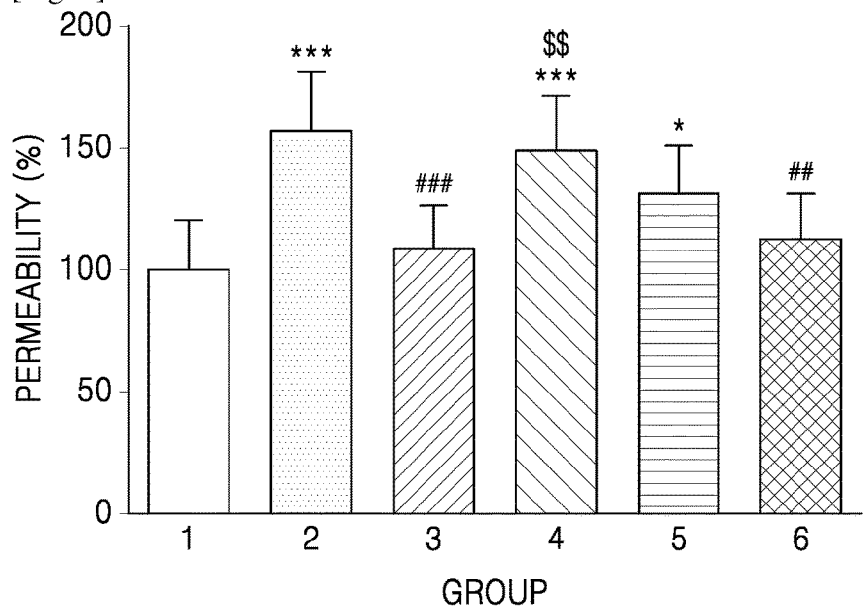
[Fig. 4]

MODIFIED DKK2 PROTEIN, NUCLEIC ACID ENCODING THE SAME, PREPARATION METHOD THEREOF, AND USE THEREOF

CROSS-REFERENCE TO RELATED APPLICATIONS

This application is a U.S. national stage of PCT/KR2016/001175, filed Feb. 3, 2016, which claims the priority from Korean Patent Application No. 10-2015-0017479, filed Feb. 4, 2015, the contents of each of which are incorporated herein by reference.

TECHNICAL FIELD

The present disclosure relates to a modified DKK2 protein which is added with a glycosyl group or has improved binding affinity, a nucleic acid encoding the same, a preparation method thereof, and use thereof.

BACKGROUND ART

Glycosylation is a process by which sugars are attached to proteins, and largely divided into N-glycosylation and O-glycosylation. Glycosylation is catalyzed by glycosyltransferase, and about 200 kinds of glycosyltransferases have been reported. The kind and structure of sugars may influence protein folding, stability, solubility, and sensitivity to protease, serum half-life, antigenicity, increase of activity, etc.

DKK2, a repressor protein of Wnt, belongs to the Dickkopf family, and has been reported to act as an inhibiting factor or stimulating factor of Wnt signaling pathways (Wu W et al., Curr. Biol., 10(24), pp. 1611-1614, 2000). DKK2 may contain into two specific cysteine-rich domains (CRD) and includes various lengths of connection regions. Particularly, DKK2 highly conserves a cystein-2 region among the Dickkopf family members which has 10 cysteine amino acids (Krupnik V E et al., Gene, 238(2), pp. 301-313, 1999). DKK2 is a protein that is hard to produce with low expression efficiency in animal cells, and thus development of therapeutic agents using DKK2 is being delayed.

Accordingly, there is a demand for DKK2 which maintains a binding affinity or has an improved binding affinity for its substrate and also shows increased expression efficiency.

DISCLOSURE OF INVENTION

Solution to Problem

An aspect provides a modified DKK2 polypeptide including one or more additional glycosylation sites, compared to an amino acid sequence of a wild-type DKK2 polypeptide.

Another aspect provides a nucleic acid encoding the modified DKK2 polypeptide.

Still another aspect provides a method of preparing the modified DKK2 polypeptide.

Still another aspect provides a pharmaceutical composition for promoting angiogenesis, the composition including the modified DKK2 polypeptide or the nucleic acid encoding the modified DKK2 polypeptide, and a pharmaceutically acceptable carrier.

Still another aspect provides a pharmaceutical composition for preventing or treating vascular permeability-related diseases, the composition including the modified DKK2 polypeptide or the nucleic acid encoding the modified DKK2 polypeptide, and a pharmaceutically acceptable carrier.

Still another aspect provides a method of promoting angiogenesis of a subject, the method including administering the modified DKK2 polypeptide or the nucleic acid encoding the modified DKK2 polypeptide to the subject.

Still another aspect provides a method of preventing or treating a vascular permeability-related disease of a subject, the method including administering the modified DKK2 polypeptide or the nucleic acid encoding the modified DKK2 polypeptide to the subject.

Advantageous Effects of Invention

According to a modified DKK2 polypeptide of an aspect, a nucleic acid encoding the same, a preparation method thereof, and use thereof, a modified DKK2 protein having additional glycosyl groups or improved binding affinity for its substrate LRP6 may be efficiently prepared, thereby being used for promoting angiogenesis or for preventing or treating vascular permeability-related diseases.

BRIEF DESCRIPTION OF DRAWINGS

These and/or other aspects will become apparent and more readily appreciated from the following description of the exemplary embodiments, taken in conjunction with the accompanying drawings in which:

FIGS. 1A and 1B are images showing the immunoblotting results of wild-type DKK2 proteins and mutant DKK2 proteins containing various tags, respectively, FIG. 1C is an image showing the immunoblotting results of DKK2 N-Gly4 and DKK2 N-Gly5 proteins containing Fc tag, and FIG. 1D is an image showing the electrophoresis result of purified proteins;

FIGS. 2A and 2B are graphs showing absorbance at 490 nm of the mutant DKK2 protein for each 200 ng of mLRP6 and hLRP6, and FIGS. 2C and 2D are graphs showing absorbance at 490 nm of the DKK2 protein for each 100 ng of mLRP6 and hLRP6;

FIGS. 3A and 3B are graphs showing fluorescence intensity (%) of retinas according to administration of the mutant DKK2 protein on Day 14 and Day 21 after administration of a test material; and FIG. 4 is a graph showing Evans blue vascular permeability (%) according to administration of the DKK2 protein.

MODE FOR THE INVENTION

An aspect provides a modified DKK2 polypeptide including one or more additional glycosylation sites, compared to an amino acid sequence of a wild-type Dickkopf (DKK)2 polypeptide.

DKK2 refers to Dickkopf-2 protein, and is also known as Dickkopf-related protein 2, cysteine-rich secreted protein 2, CRSP2, CRISPY2, or CRSP 2 protein. DKK2 is a protein that in humans is encoded by the DKK2 gene. This gene encodes a protein that is a member of the Dickkopf family. It is known that DKK2, a secreted protein, contains two cysteine-rich regions and is involved in embryonic development through its interactions with a Wnt signaling pathway. In addition, it may act as either an agonist or antagonist of Wnt/beta-catenin signaling, depending on the cellular context and the presence of a co-factor kremen 2. DKK2 may bind with low-density lipoprotein receptor-related protein 6 (LRP6).

The wild-type DKK2 polypeptide may be a wild-type DKK2 precursor polypeptide. The wild-type DKK2 precursor polypeptide may be a polypeptide having an amino acid sequence (SEQ ID NO: 1) of Genbank accession no. NP_055236.1 in human or an amino acid sequence of Genbank accession no. NP_064661.2 in mouse. The wild-type DKK2 precursor polypeptide may include a signal peptide, and the signal peptide may be cleaved by co-translational modification or post-translational modification. The wild-type DKK2 polypeptide may be mature DKK2. The mature DKK2 may be a polypeptide including an amino acid sequence obtained by removing an amino acid sequence (signal peptide or leader peptide) at positions 1 to 33 from the N-terminus of the amino acid sequence of SEQ ID NO: 1, or a polypeptide including an amino acid sequence of SEQ ID NO: 3. The wild-type DKK2 precursor polypeptide may be encoded by a nucleic acid having a nucleotide sequence (SEQ ID NO: 4) of Genbank accession no. NM_014421 in human and a nucleic acid having a nucleotide sequence of Genbank accession no. NM_020265 in mouse.

The glycosylation refers to a reaction of transferring glycosyl groups to proteins. The glycosylation is catalyzed by glycosyltransferase. The glycosylation may be N-glycosylation, O-glycosylation, phospho-serine glycosylation, C-mannosylation, glypiation, or a combination thereof. N-glycosylation refers to attachment of sugar molecules to the amide group of asparagine.

The glycosylation site refers to a site to which a sugar molecule or a glycosyl group may be attached. For example, the glycosylation site may be an asparagine residue in a consensus sequence of Asn-Xaa-Ser/Thr, which is N-glycosylation site. Asn represents asparagine, Xaa represents an amino acid excluding proline, Ser represents serine, Thr represents threonine, and Ser/Thr represents serine or threonine. The Asn-Xaa-Ser/Thr represents a polypeptide composed of asparagine-amino acid (excluding proline)-serine or amino acid from the N-terminus. A sugar molecule is attached to asparagine of Asn-Xaa-Ser/Thr. The wild-type DKK2 precursor polypeptide may include one glycosylation site at position 36 from the N-terminus.

The glycosylation site of the modified DKK2 polypeptide may be introduced by substituting asparagine (Asn, N) for one or more amino acids selected from the group consisting of 5I, 31G, 96P, 110D, 44P, 2L, 45C, 57C, 62Q, 63G, 85P, 6K, 98T, 101I, 11G, 121H, 135P, 138K, 151L, 152R, 166F, 187K, 203G, 211D, 213T, and 214Y in the amino acid sequence of SEQ ID NO: 3. The numeral represents the position of the amino acid from the N-terminus of the amino acid sequence of SEQ ID NO: 3, and the alphabetic character represents 1 letter code of the amino acid. For example, '5I' represents isoleucine at position 5 from the N-terminus of the amino acid sequence of SEQ ID NO: 3.

The modification may be substitution of one or more of amino acids.

The modified DKK2 polypeptide may be a DKK2 polypeptide, in which a glycosyl group is additionally introduced by introduction of the glycosylation site. Although the modified DKK2 polypeptide may vary in sugar linkage, sugar composition, glycosyl structure, or a combination thereof, glycosylation occurs at the same glycosylation site of the amino acid sequence of the DKK2 polypeptide. As a result, intracellular expression efficiency may be increased. For example, although the modified DKK2 polypeptide may vary in the sugar linkage (e.g., N-glycosylation and O-glycosylation), sugar composition (e.g., difference in the degree of sialylation), and glycolstructure according to the kind of a host cell in which the modified DKK2 polypeptide is expressed, glycosylation may occur at the same glycosylation site of the DKK2 polypeptide.

The modified DKK2 polypeptide may be a polypeptide including one or more amino acid sequences selected from the group consisting of SEQ ID NOS: 5 to 30.

A tag may be further included at the N-terminus or C-terminus of the modified DKK2 polypeptide. The tag may be a polypeptide which is attached to the DKK2 polypeptide in order to facilitate expression, purification, detection, etc. The tag may be, for example, an Fc (fragment crystallizable) region, a poly-histidine peptide, or a combination thereof. The Fc region may be a human Fc region, a mouse Fc region, etc. The Fc region may be a polypeptide encoded by a nucleotide sequence of SEQ ID NO: 48. The Fc region may be a polypeptide consisting of an amino acid sequence of SEQ ID NO: 49. The tag may be known to those skilled in the art.

The modified DKK2 polypeptide may further include a signal peptide at the N-terminus. The signal peptide refers to a peptide (about 5 to 30 amino acids long) present at the N-terminus of the majority of newly synthesized proteins that are destined towards the secretory pathway. The signal peptide may be an amino acid sequence at positions 1 to 33 from the N-terminus of the amino acid sequence of SEQ ID NO: 1 or a polypeptide including the amino acid sequence of SEQ ID NO: 2.

The modified DKK2 polypeptide may be a polypeptide having an addition of glycosyl groups, an increase in LRP6 binding affinity, or a combination thereof, compared to the wild-type DKK2 polypeptide. The addition of glycosyl groups in the modified DKK2 polypeptide may be an increase in the amount of glycosyl groups, compared to that of the wild-type DKK2 polypeptide as a control group. Due to the addition of glycosyl groups, the amount of the modified DKK2 polypeptide may be increased in cells, compared to the amount of the wild-type DKK2 polypeptide. The amount of a transcript encoding the modified DKK2 polypeptide may be increased in cells, compared to that of a transcript encoding the wild-type DKK2 polypeptide. The increase in the amount of the polypeptide or transcript may mean an increase in the intracellular expression efficiency of the polypeptide. The binding affinity of the modified DKK2 polypeptide for LRP6 may be increased, compared to that of the wild-type DKK2 polypeptide. As the binding affinity is higher, a dissociation constant (KD) may be lower. The dissociation constant of the modified DKK2 polypeptide for LRP6 may be, for example, about 0.1 nM to about 100 nM, about 1 nM to about 50 nM, about 2 nM to about 40 nM, about 3 nM to about 30 nM, about 4 nM to about 20 nM, about 5 nM to about 10 nM, or about 5.5 nM.

Another aspect provides a nucleic acid encoding the modified DKK2 polypeptide.

The modified DKK2 polypeptide is the same as described above.

The nucleic acid may include any one nucleotide sequence selected from the group consisting of SEQ ID NOS: 43 to 47. The nucleic acid may further include a nucleotide sequence encoding the tag at the 5'-terminus or 3'-terminus of the nucleic acid encoding the modified DKK2 polypeptide. The nucleic acid may further include a nucleotide sequence encoding the signal peptide at the 5'-terminus of the nucleic acid encoding the modified DKK2 polypeptide. The nucleic acid may be operably linked to a gene expression regulatory element such as a promoter, an operator, an enhancer and/or a transcription terminator.

Another aspect provides a method of preparing the modified DKK2 polypeptide, the method including culturing cells which are introduced with a vector including the nucleic acid encoding the modified DKK2 polypeptide in the presence of a culture medium to obtain a culture product; and obtaining the modified DKK2 polypeptide from the culture product.

The modified DKK2 polypeptide, and the nucleic acid encoding the modified DKK2 polypeptide are the same as described above.

The cell may be a eukaryotic cell. For example, the cell may be an animal cell. The cell may be, for example, an embryonic kidney cell, an ovarian cell, a myeloma cell, or a retina-derived cell. The embryonic kidney cell may be a human embryonic kidney (HEK) 293 cell or a baby hamster kidney (BHK) cell. The ovarian cell may be a Chinese hamster ovary cell (CHO) cell. The myeloma cell may be an NS0 cell or an SP2/0 cell. The retina-derived cell may be a PerC6 cell. According to the kind of the cell, DKK2 polypeptides varying in the sugar linkage (e.g., N-glycosylation and O-glycosylation), sugar composition (e.g., difference in the degree of sialylation), and glycosyl structure may be expressed.

The method may further include introducing a vector including the nucleic acid encoding the modified DKK2 polypeptide into cells.

The vector may be, for example, a plasmid, a viral vector, a cosmid, or an artificial chromosome. The vector may be an expression vector including a promoter sequence. The vector may be a vector capable of expressing a target gene in eukaryotic cells.

The introducing refers to introducing the nucleic acid into cells. The introducing may be, for example, introducing by transformation, transjection, transduction, conjugation, or electroporation.

The method includes culturing the introduced cells in the presence of a culture medium to obtain a culture product.

The culture medium refers to a medium containing components which are required for or function to promote survival or proliferation of cells. The culture medium may be selected by those skilled in the art according to the kind of cells.

The culturing may be performed by incubation using a method known to those skilled in the art. The culturing may be performed, for example, under conditions of a temperature of about 37° C. and 5% $CO_2$.

The method includes obtaining the modified DKK2 polypeptide from the culture product. The culture product may be a culture broth excluding the cultured cells or the cultured cells.

The obtaining the modified DKK2 polypeptide may include obtaining and lysing the cells, and purifying or filtering the polypeptide. The method of obtaining the polypeptide may be known to those skilled in the art.

Still another aspect provides a pharmaceutical composition for promoting angiogenesis, the composition including the modified DKK2 polypeptide or the nucleic acid encoding the modified DKK2 polypeptide, and a pharmaceutically acceptable carrier.

The modified DKK2 polypeptide, and the nucleic acid encoding the modified DKK2 polypeptide are the same as described above.

The angiogenesis refers to a process by which new blood vessels are formed. Angiogenesis includes a process by which new blood vessels grow from pre-existing vessels. Angiogenesis is a normal and important process in wound healing and granulation tissue as well as growth and development. In addition, angiogenesis is a fundamental step in the transition of tumors from a dormant state to a malignant state.

The promoting may be achieved in vitro or in vivo. The promoting may be inducing formation or regeneration of new blood vessels in a subject having an ischemic vascular disease.

The pharmaceutical composition may be a pharmaceutical composition for preventing or treating ischemic vascular diseases. The ischemic vascular disease may be, for example, burn, psoriasis, ulcer, ischemia, ischemic heart disease, ischemic cerebrovascular disease, or erectile dysfunction.

Still another aspect provides a pharmaceutical composition for preventing or treating vascular permeability-related diseases, the composition including the modified DKK2 polypeptide or the nucleic acid encoding the modified DKK2 polypeptide, and a pharmaceutically acceptable carrier.

The modified DKK2 polypeptide, and the nucleic acid encoding the modified DKK2 polypeptide are the same as described above.

The vascular permeability-related disease refers to a disease having a symptom caused by the increased leakage of body fluids into the surrounding tissues due to increased vascular permeability. The vascular permeability-related diseases may be, for example, diabetic retinopathy, diabetic macular edema, macular edema following retinal vein occlusion, macular degeneration (e.g., neovascular (Wet) age-related macular degeneration), choroidal neovascularization, glaucoma retinitis pigmentosa, retinopathy of prematurity (ROP), glaucoma, corneal dystrophy, retinoschises, Stargardt's disease, autosomal dominant druzen, Best's macular dystrophy, cystoid macular edema, ischemic retinopathy, inflammation-induced retinal degenerative disease, X-linked juvenile retinoschisis, Malattia Leventinese (ML) or Doyne honeycomb retinal dystrophy.

As used herein, the term "prevention" means all of the actions by which the occurrence of disease is restrained or retarded by administration of the pharmaceutical composition. The term "treatment" means all of the actions by which the symptoms have taken a turn for the better or been modified favorably by administration of the pharmaceutical composition.

The pharmaceutical composition may include a pharmaceutically acceptable carrier. The carrier includes an excipient, a diluent, or an auxiliary substance. The carrier may be, for example, selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, a physiological saline solution, a buffer such as PBS, methylhydroxy benzoate, propylhydroxy benzoate, talc, magnesium stearate and mineral oil. The composition may include a filler, an anti-agglutinant, a lubricant, a wetting agent, a flavor, an emulsifier, a preservative, etc.

The pharmaceutical composition may be prepared in any formulation. The composition may be formulated in an oral dosage form (e.g., powder, tablet, capsule, syrup, pill, granule) or a parenteral dosage form (e.g., injectable formulation). In addition, the composition may be prepared in systemic dosage forms or topical dosage forms.

The pharmaceutical composition may include an effective amount of the modified DKK2 polypeptide or the nucleic acid encoding the modified DKK2 polypeptide. The effective amount may be properly selected according to a cell or a subject selected by those skilled in the art. The effective amount may be determined depending on the severity of disease, a patient's age, body weight, health conditions, gender, and drug sensitivity, administration time, administration route, excretion rate, treatment period, and drugs blended with or co-administered with the composition, and other factors well known in the medical field. The effective amount may be about 0.5 µg to about 2 g, about 1 µg to about 1 g, about 10 µg to about 500 mg, about 100 µg to about 100 mg, about 1 mg to about 50 mg, based on the pharmaceutical composition.

An administration dose of the pharmaceutical composition may be, for example, in the range of about 0.001 mg/kg to about 100 mg/kg, about 0.001 mg/kg to about 10 mg/kg, about 0.001 mg/kg to about 1 mg/kg, about 0.005 mg/kg to about 1 mg/kg, about 0.01 mg/kg to about 1 mg/kg, or about 0.1 mg/kg to about 1 mg/kg per adult once a day, several times a day, twice or three times a week, once to four times a month, one to twelve times a year.

Still another aspect provides a method of promoting angiogenesis of a subject, the method including administering the modified DKK2 polypeptide or the nucleic acid encoding the modified DKK2 polypeptide to the subject.

Still another aspect provides a method of preventing or treating a vascular permeability-related disease of a subject, the method including administering the modified DKK2 polypeptide or the nucleic acid encoding the modified DKK2 polypeptide to the subject.

The modified DKK2 polypeptide, the nucleic acid encoding the modified DKK2 polypeptide, angiogenesis, promoting, vascular permeability-related disease, prevention, and treatment are the same as described above.

The subject may be a mammal, for example, human, cow, horse, pig, dog, sheep, goat, or cat. The subject may be a subject having an ischemic disease or high possibility of having an ischemic disease. The subject may be a subject having a vascular permeability-related disease or high possibility of having a vascular permeability-related disease.

The administration may be performed directly to a subject by any means, for example, oral, intravenous, intramuscular, transdermal, mucosal, intranasal, intratracheal, or subcutaneous administration. The administration may be topical or systemic administration.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

Example 1. Preparation and Identification of N-Glycosylated Mutant DKK2 Protein 1. Prediction of N-Glycosylation Site of DKK2 Protein An amino acid sequence (SEQ ID NO: 3) of a wild-type DKK2 protein has an N-glycosylation site at position 3 from the N-terminus. To artificially induce the N-glycosylation in the wild-type DKK2 protein, the N-glycosylation site of the wild-type DKK2 protein was predicted using NetNGlyc1.0 server (www.cbs.dtu.dk/services/NetNGlyc/).

A total of 26 types of the N-glycosylation site of the DKK2 protein were predicted from the NetNGlyc1.0 server, and the result is given in Table 1. In Table 1, the amino acid represents an amino acid of the wild-type DKK2 protein (SEQ ID NO: 3) and asparagine (Asn, N) mutated therefrom, and the numeral represents the position of the mutated amino acid from the N-terminus of the wild-type DKK2 protein.

TABLE 1

| Mutant DKK2 protein | Amino acid modification for N-glycosylation | Amino acid sequence |
|---|---|---|
| DKK2 N-Gly1 | 5I -> 5N | SEQ ID NO: 5 |
| DKK2 N-Gly2 | 31G -> 31N | SEQ ID NO: 6 |
| DKK2 N-Gly3 | 96P -> 96N | SEQ ID NO: 7 |
| DKK2 N-Gly4 | 110D -> 110N | SEQ ID NO: 8 |
| DKK2 N-Gly5 | 44P -> 44N | SEQ ID NO: 9 |
| DKK2 N-Gly6 | 2L -> 2N | SEQ ID NO: 10 |
| DKK2 N-Gly7 | 45C -> 45N | SEQ ID NO: 11 |
| DKK2 N-Gly8 | 57C -> 57N | SEQ ID NO: 12 |
| DKK2 N-Gly9 | 62Q -> 62N | SEQ ID NO: 13 |
| DKK2 N-Gly10 | 63G -> 63N | SEQ ID NO: 14 |
| DKK2 N-Gly11 | 85P -> 85N | SEQ ID NO: 15 |
| DKK2 N-Gly12 | 6K -> 6N | SEQ ID NO: 16 |
| DKK2 N-Gly13 | 98T -> 98N | SEQ ID NO: 17 |
| DKK2 N-Gly14 | 101I -> 101N | SEQ ID NO: 18 |
| DKK2 N-Gly15 | 11G -> 11N | SEQ ID NO: 19 |
| DKK2 N-Gly16 | 121H -> 121N | SEQ ID NO: 20 |
| DKK2 N-Gly17 | 135P -> 135N | SEQ ID NO: 21 |
| DKK2 N-Gly18 | 138K -> 138N | SEQ ID NO: 22 |
| DKK2 N-Gly19 | 151L -> 151N | SEQ ID NO: 23 |
| DKK2 N-Gly20 | 152R -> 152N | SEQ ID NO: 24 |
| DKK2 N-Gly21 | 166F -> 166N | SEQ ID NO: 25 |
| DKK2 N-Gly22 | 187K -> 187N | SEQ ID NO: 26 |
| DKK2 N-Gly23 | 203G -> 203N | SEQ ID NO: 27 |
| DKK2 N-Gly24 | 211D -> 211N | SEQ ID NO: 28 |
| DKK2 N-Gly25 | 213T -> 213N | SEQ ID NO: 29 |
| DKK2 N-Gly26 | 214Y -> 214N | SEQ ID NO: 30 |

Among 26 types of the N-glycosylation site candidates of DKK2 protein, 5 types of mutant DKK2 proteins showing a high N-glycosylation potential in the NetNGlyc1.0 server were selected, and protein production efficiency was examined.

The N-glycosylation potentials of the selected 5 types of mutant DKK2 proteins are given in the following Table 2.

TABLE 2

| Mutant DKK2 protein | Potential of N-glycosylation |
|---|---|
| DKK2 N-Gly1 | 0.7342 |
| DKK2 N-Gly2 | 0.7206 |
| DKK2 N-Gly3 | 0.7010 |
| DKK2 N-Gly4 | 0.7541 |
| DKK2 N-Gly5 | 0.7372 |

2. Verification of Production Efficiency of Selected N-Glycosylated DKK2 Protein To express 5 types of DKK2 proteins selected in Example 1.1, each of them was inserted into a high-efficiency expression vector to examine protein production efficiency by a transient expression system.

(1) Polymerase Chain Reaction

A wild-type DKK2 native form (Genbank accession no. NP_055236.1, SEQ ID NO: 3) (provided by medpacto, Inc., Korea) was used as a template.

Nucleotide sequences of primers designed for DKK2 N-glycosylation are given in Table 3.

TABLE 3

| Amplification target | Primer | Nucleotide sequence |
|---|---|---|
| DKK2 N-Gly1 | Forward primer | 5'-ggcatgtgctgcaacagtacccgctgcaataatggcatct-3' (SEQ ID NO: 31) |
| | Reverse primer | 5'-gcagcgggtactgttgcagcacatgccatctcggtggc-3' (SEQ ID NO: 32) |
| DKK2 N-Gly2 | Forward primer | 5'-aatctaggaagaaatcacactaagatgtcacatataaaaggg-3' (SEQ ID NO: 33) |
| | Reverse primer | 5'-catcttagtgtgatttcttcctagattctgccatcccaagtc-3' (SEQ ID NO: 34) |
| DKK2 N-Gly3 | Forward primer | 5'-catcagggggaaaactgtaccaaacaacgcaagaagggttc-3' (SEQ ID NO: 35) |
| | Reverse primer | 5'-ttgttttggtacagttttcccctgatggagcactggtttg-3' (SEQ ID NO: 36) |
| DKK2 N-Gly4 | Forward primer | 5'-atcccggctctgaatggtactcggcacagagatcgaaac-3' (SEQ ID NO: 37) |
| | Reverse primer | 5'-gtgccgagtaccattcagagccgggatgtgaggggttaa-3' (SEQ ID NO: 38) |
| DKK2 N-Gly5 | Forward primer | 5'-gggcaggcctacaattgtagcagtgataaggagtgtgaagtt-3' (SEQ ID NO: 39) |
| | Reverse primer | 5'-atcactgctacaattgtaggcctgccccaggtttttgcc-3' (SEQ ID NO: 40) |
| Vector | Forward primer | 5'-accggtggtaccgccaccatgggatggag-3' (SEQ ID NO: 41) |
| | Reverse primer | 5'-ggatttatacaaggaggagaaaatgaaag-3' (SEQ ID NO: 42) |

For polymerase chain reaction, a mixture of the following composition was prepared.

100 ng of template 2.5 unit of pfu DNA polymerase (SPX16-RS500, Solgent Co., Ltd.)

10 pmol of forward primer 10 pmol of reverse primer

1 µl of 10 mM dNTP

5 µl of 10× pfu polymerase buffer

50 µl of total volume

A prepared mix was incubated at 95° C. for 2 minutes, and then 30 cycles, with 1 cycle consisting of at 95° C. for 20 seconds, at 64° C. for 40 seconds, and at 72° C. for 1 minute, were repeated, followed by incubation at 72° C. for 10 minutes. Consequently, mutant DKK2 nucleic acids thus amplified were obtained.

(2) Cloning of Amplification Products and Examination of Transient Protein Expression in Host Cells The amplified mutant DKK2 nucleic acid or the wild-type DKK2 nucleic acid was incubated in the presence of 10 units of restriction enzyme SfiI (Cat. No. R033S, Enzynomics, Korea) and 1× reaction buffer at 50° C. for 6 hours. A reaction product was electrophoresed on an agarose gel, and the nucleic acid to be inserted into a vector was purified using a gel Purification kit (Cat. No. 1014876, QIAGEN, USA). A mammalian expression vector N293F-FC (ATP-100, ANRT) and the purified nucleic acid were mixed at a weight ratio of 1:3, followed by incubation in the presence of 10 units of T4 DNA ligase (Cat. No. M001S, Enzynomics, Korea) and 1× reaction buffer at 22° C. for 4 hours or longer.

A reaction product was transformed into E. coli, and a nucleotide sequence encoding DKK2 N-Gly1, DKK2 N-Gly2, DKK2 N-Gly3, DKK2 N-Gly4, or DKK2 N-Gly5 (SEQ ID NO: 43 to 47, respectively) was examined by sequencing analysis. Clones including the N293F-FC vector which was introduced with the mutant DKK2 nucleic acid were selected.

An N293F-FC-mDKK2 vector introduced with the mutant DKK2 nucleic acid (mDKK2) was obtained from the selected clones. Fc nucleic acid was a nucleic acid (SEQ ID NO: 48) encoding an Fc fragment of human immunoglobulin G1.

A mammalian HEK293F suspension cell was seeded at a density of $5 \times 10^5$ cells/ml in Free style media (Cat. No. 1508027, Invitrogen, USA) and cultured under conditions of 37° C. and 5% $CO_2$. The cells were cultured until the density of the cells reached about $1 \times 10^6$ cell/ml (about 24 hours).

25 µg of N293F-FC vector introduced with the mutant DKK2 nucleic acid, 50 µg of polyethyleneimine (PEI) (Cat. No. 23966, Polysciences, USA) and 600 µl of PMI medium (Cat. No. sh30027.01, Hiclone, USA) were mixed, and incubated at room temperature for 20 minutes. A reaction product was added to the cultured HEK293F cells and cultured under conditions of 37° C. and 5% $CO_2$ for about 5 days. Thereafter, to obtain a water-soluble protein secreted by the cells, the cells were removed from the culture product and a culture broth excluding the cells was only collected.

200 µl of culture broth was subjected to 10% SDS-PAGE, followed by immunoblotting. Since the obtained mutant DKK2 protein and the wild-type DKK2 protein included FC-TAG, HIS-TAG, or mFc-tag at their N-terminus, anti-Fc-HRP (Cat. No. 31414, PIERCE, USA) diluted at 1:4000, anti-HIS-HRP (Cat. No. A7058, SIGMA, USA) diluted at 1:2000, or anti-mFc (Cat. No. 31430, PIERCE, USA) diluted at 1:2000 was used. As a color development reagent, an ECL KIT (Cat. No. 0034077 GE USA) was used to obtain images.

FIG. 1A shows the immunoblotting result of wild-type DKK2 proteins containing various tags (exposure time: 1 minute, M: marker (KDa), 1: N-Fc-DKK2, 2: N-Fc(IgG4)-DKK2, 3: N-His-DKK2, 4: N-mFc-DKK2). As shown in FIG. 1A, no wild-type DKK2 proteins were detected even though exposed for 1 minute. Therefore, it was confirmed that the wild-type DKK2 proteins were hardly expressed.

FIG. 1B shows the immunoblotting result of mutant DKK2 proteins containing various tags (exposure time: 1 minute (left) or 1 second (right), M: marker (KDa), 1: N-mFc-DKK2-gly1, 2: N-mFc-DKK2-gly2, 3: N-mFc-DKK2-gly3, 4: N-Fc4-DKK2-gly1, 5: N-His-DKK2-gly1, 6: N-Fc-DKK2-gly1, 7: N-His-DKK2-gly2, 8: N-Fc4-

DKK2-gly2, 9: N-Fc-DKK2-gly2, 10: N-Fc-DKK2-gly3, 11: N-His-DKK2-gly3, 12: N-Fc4-DKK2-gly3). As shown in FIG. 1B, the mutant DKK2 protein containing Fc-tag was detected, whereas the mutant DKK2 proteins containing tags other than Fc were hardly detected. Therefore, it was confirmed that the mutant DKK2 protein containing Fc tag showed improved expression efficiency. The expressed protein was purified using a disposable open column and its concentration was measured.

Since the protein containing Fc tag shows improved expression efficiency, Fc tag-containing DKK2 N-Gly4 and DKK2 N-Gly5 proteins were obtained. The obtained proteins were subjected to immunoblotting and the result is shown in FIG. 1C (exposure time: 1 second (left) or 30 seconds (right), M: marker (KDa), 1: N-Fc-DKK2-gly4, 2: N-Fc-DKK2-gly5). As shown in FIG. 1C, it was confirmed that N-Fc-DKK2-N-Gly4 showed higher expression efficiency than N-Fc-DKK2-N-Gly5.

(3) Mass-Production and Purification of Protein

As described in Example 1(2), cells transformed with the vector containing Fc tag and mutant DKK2 nucleic acid were selected. The selected cells were cultured under conditions of 37° C. and 5% $CO_2$ for about 5 days. The culture broth excluding cells was centrifuged at room temperature at a speed of 4800 rpm for 20 minutes to obtain a supernatant. Filtration was performed using a 0.22 μm filter (Cat. No. PR02890, Millipore, USA). 5 ml-column packed with protein A beads (Cat. No. 17-1279-03, GE healthcare, Sweden) was prepared and a filtrate was applied to the beads at 4° C. overnight at a rate of 0.9 ml/min. The beads were washed with 100 ml or more of PBS (Phosphate Buffered Saline) (Cat. No. 70011, Gibco, USA). Thereafter, 0.1 M glycine-HCl (Cat. No. G7126, Sigma, USA) was applied to the beads to elute 6 fractions. 1 M Tris (Cat. No. T-1503-5KG, Sigma, USA) (pH 9.0) was added to neutralize the fractions. Proteins in the fractions were quantified, and fractions containing the proteins were collected. The fractions were applied to amicon ultra (Cat. No. UFC805024, Millipore, USA) and centrifuged according to the manufacturer's instruction. 1×PBS was added to a concentrate and centrifugation was repeated three times to be replaced by PBS as a storage buffer.

The purified protein was quantified. The amount of N-Fc-DKK2-gly1 was 130 μg in 40 ml of culture broth, the amount of N-Fc-DKK2-gly2 was 860 μg in 40 ml of culture broth, the amount of N-Fc-DKK2-gly3 was 150 μg in 40 ml of culture broth, the amount of N-Fc-DKK2-gly4 was 462 μg in 40 ml of culture broth, and the amount of N-Fc-DKK2-gly5 was 27 μg in 40 ml of culture broth. Among the mutant DKK2 proteins introduced with N-glycosylation sites, N-Fc-DKK2-Gly2 showed the highest expression efficiency and N-Fc-DKK2-Gly4 showed the next highest expression efficiency. Therefore, the mutant DKK2 protein introduced with the N-glycosylation site was highly expressed, compared to the wild-type DKK2 protein, and N-Fc-DKK2-Gly2 and N-Fc-DKK2-Gly4 showed expression efficiency about 80 times and about 50 times higher than that of the wild-type DKK2, respectively.

To examine purity of the purified protein, 3 μg of the protein was electrophoresed by 10% SDS-PAGE, and the result is shown in FIG. 1D (M: marker (KDa), 1: N-Fc-DKK2-gly1, 2: N-Fc-DKK2-gly2, 3: N-Fc-DKK2-gly3, 4: N-Fc-DKK2-gly4, 5: N-Fc-DKK2-gly5). As shown in FIG. 1D, N-Fc-DKK2-gly2 and N-Fc-DKK2-gly4 were found to be similar to each other in purity.

3. Examination of Binding Affinity of Mutant DKK2 Protein

Since DKK2 protein is known to bind to mouse LRP6 (mLRP6) and human LRP6 (hLRP6), the binding affinities of the wild-type DKK2 and the mutant DKK2 proteins for LRP6 were examined.

In detail, 200 ng of hLRP6 protein (Cat. No. 1505-LR-025, R&D, USA) or mLRP6 protein (Cat. No. 2960-LR-025, R&D, USA) was applied to each well of ELISA plate (Cat. No. 439454, Nunc, Denmark), and incubated at 4° C. overnight to coat the plate with the protein. 200 μl of 4% (w/v) skim milk (Cat. No. 232100, Difco, France)/1×PBS was applied to the wells of ELISA plate and incubated at room temperature for about 1 hour for blocking. Thereafter, the blocking solution was removed from the ELISA plate.

Each purified DKK2 protein and 100 μl of 1% (w/v) skim milk/1×PBS were mixed to prepare 100 nM of DKK2 protein, and 100 nM of DKK2 protein was subjected to ¼ serial dilution. The diluted protein was applied to the prepared ELISA plate, and incubated at room temperature for about 2 hours. Thereafter, the plate was washed with 200 μl of PBST five times.

2 μl of anti-Human Fc-HRP (Cat. No. 31413, Thermo, USA) antibody was mixed with 4 ml of PBS containing 1% (w/v) skim milk, and 200 μl of this mixture was added to each well of ELISA plate and incubated at room temperature for 1 hour. Thereafter, the secondary antibody of the ELISA plate was removed, and the plate was washed with 200 of PBS five times. 10 μl of $H_2O_2$ solution (Cat. No. H1009-100ML, Sigma, USA), 10 ml of PC buffer (5.1 g of citric acid monohydrate, 7.3 g of sodium phosphate/L (pH 5.0)), and one tablet of OPD (Cat. No. P8787-100TAB, Sigma, USA) were mixed to prepare a mixture, and a total volume of 100 μl of the mixture was added to each well. Incubation was performed at room temperature in the dark for 10 minutes, followed by color development. Thereafter, 50 μl of a stop buffer was added to each well to terminate the color development. Absorbance at 490 nm was measured using an ELISA reader, and a dissociation constant $K_D$ value (M) was calculated from the measured absorbance.

FIG. 2A shows absorbance at 490 nm of the mutant DKK2 protein for 200 ng of mLRP6, and FIG. 2B shows absorbance at 490 nm of the mutant DKK2 protein for 200 ng of hLRP6 (■: N-Fc-DKK2-Gly1, ▲: N-Fc-DKK2-Gly2, ▼: N-Fc-DKK2-Gly3, ♦: N-Fc-DKK2-Gly4, ■: N-Fc-DKK2-Gly5). As shown in FIGS. 2A and 2B, N-Fc-DKK2-Gly4 showed the most improved binding affinity for mLRP6 and hLRP6. It was confirmed that N-Fc-DKK2-Gly2 showed the highest expression efficiency, but its binding affinity for mLRP6 and hLRP6 was not high. Accordingly, N-Fc-DKK2-Gly4 was confirmed to be a mutant DKK2 protein showing improved expression efficiency and high binding affinity for mLRP6 and hLRP6.

To compare the binding affinity for mLRP6 and hLRP6 between N-Fc-DKK2-Gly4 and wild-type DKK2 (Cat. No. 6628-DK-010, R&D, USA), ELISA was performed in the same manner as above, except that 100 ng of LRP6 was used.

FIG. 2C shows absorbance at 490 nm of the DKK2 protein for 100 ng of mLRP6 and FIG. 2D shows absorbance at 490 nm of the DKK2 protein for 100 ng of hLRP6 (■: N-Fc-DKK2-Gly4, ▲: wild-type DKK2). Dissociation constant ($K_D$) and $R^2$ value calculated from the measured absorbance are given in Table 4.

TABLE 4

| | mLRP6 | | hLRP6 | |
|---|---|---|---|---|
| | DKK2 N-Gly4 | Wild-type DKK2 | DKK2 N-Gly4 | Wild-type DKK2 |
| $K_D(M)$ | $1 \times 10^{-8}$ | $2.7 \times 10^{-7}$ | $5.5 \times 10^{-9}$ | $9.0 \times 10^{-8}$ |
| $R^2$ | 0.99 | 0.86 | 0.99 | 0.98 |

It was confirmed that the binding affinity of N-Fc-DKK2-Gly4 for hLRP6 and mLRP6 were about 5 to about 10 times higher than that of the wild-type DKK2.

4. Examination of Angiogenesis by Mutant DKK2 Protein

In order to examine whether the mutant DKK2 protein is able to induce angiogenesis, corneal pocket assay (CPA) was performed.

C57BL6 mice (male, 9-week old, weighing 21.81 g-23.81 g) were purchased from Orientbio Inc. (Korea), and then acclimated for about 7 days at an animal facility where experiments were performed.

To administer a drug to the cornea, a drug pellet was prepared. In detail, 10 g of sucrose octasulfate-aluminum complex (S0652, Sigma-aldrich) was dissolved in 100 ml of PBS (Phosphate Buffer Saline) to prepare a 10% (w/v) sucralfate solution. 12 g of poly-2-hydroxyethyl methacrylate (P3932, Sigma-aldrich) was dissolved in 100 ml of absolute ethanol to prepare a 12% (w/v) poly-HEMA solution. A parafilm was placed in a Petri dish and left under UV for about 15 minutes. 5 µl of 12% (w/v) poly-HEMA solution, 1 µl of 10% (w/v) sucralfate solution, and 4 µl of the drug were mixed. Each 0.2 µl of this mixture was dispensed on the parafilm and the dispensed pellets were dried at room temperature for about 1 to 2 hours. The dried pellets were stored in a refrigerator before use.

The acclimated mice (male, 10-week old, weighing 2123.43 g-26.11 g) were divided into 2 groups (n=5 per group), and anesthetized by intraperitoneal injection of a 4:1(v/v) mixture of ketamine and xylazine ((Rompun™), Bayer AG, Germany). About 10 minutes later, 0.5% proparacaine was dropped into their corneas. With a von Graefe cataract knife, a micropocket was made at the cornea under a microscope. The prepared pellets were implanted into the corneal micropocket (Day 1). To prevent infection, terramycin ophthalmic ointment was applied to the eye. As a test material, N-Fc-DKK2-Gly4 was used, and 475 ng of N-Fc-DKK2-Gly4 per mouse was administered. As a negative control group, PBS was used. Thereafter, the corneas were examined under a microscope, and angiogenesis and structural features were observed by an image analyzer. No angiogenesis was detected in the negative control group, whereas angiogenesis was detected in the N-Fc-DKK2-Gly4-treated group on Day 5. The area (mm²) of the angiogenesis in the N-Fc-DKK2-Gly4-treated group was calculated and the result is given in Table 5.

TABLE 5

| No. | Day 1 | Day 3 | Day 5 | Day 7 |
|---|---|---|---|---|
| 1 | 0.00 | 0.00 | 0.00 | 0.00 |
| 2 | 0.00 | 0.00 | 0.00 | 0.00 |
| 3 | 0.00 | 0.00 | 0.00 | 0.00 |
| 4 | 0.00 | 0.00 | 0.02 | 0.03 |
| 5 | 0.00 | 0.00 | 0.06 | 0.13 |

As shown in Table 5, angiogenesis was observed in the N-Fc-DKK2-Gly4-treated group, compared to the negative control group.

5. Diabetic Retinopathy-Improving Effect of Mutant DKK2 Protein

It was examined whether the mutant DKK2 protein is able to improve symptoms of diabetic retinopathy.

Chinchilla rabbits (male, 10-11-week old, weighing 2.0 kg-2.5 kg) were purchased from DREAMBIO Inc. (Korea), and then acclimated for about 7 days at an animal facility where experiments were performed. Alloxan monohydrate (Sigma-Aldrich Co.) as a diabetic inducer were administered to the ear vein of the acclimated rabbits Blood glucose levels were measured at 7 days after administration (Day 0), and animals having the blood glucose level of 300 mg/dL were selected. The selected rabbits were randomly divided so that the average glucose blood level of each group was equally distributed.

The diabetes-induced rabbit were anesthetized by intravenous injection of Zoletil 50 (VIRBAC, France) and xylazine (Rompun™, Bayer AG, Germany). As a test material, N-Fc-DKK2-Gly4 (in PBS) was administered by intravitreal injection on Day 0 (7 days after Alloxan administration) and Day 7 once a day in a total amount of 10 µl/eye for two administrations. As a normal control group, PBS was injected instead of Alloxan. As a diabetes control group, Alloxan was administered, and as a positive control group, EYLEA® (Bayer Korea Ltd.) was administered by intravitreal injection on Day 0 in an amount of 50 µl/eye once. The administered drugs are given in the following Table 6.

TABLE 6

| Group | Number of animal | Administration material | One dose and administration frequency | Note |
|---|---|---|---|---|
| 1 | 7 | PBS | 0 | Non-treated |
| 2 | 7 | PBS | 0 | Diabetes-induced |
| 3 | 7 | EYLEA | 2000 µg, once | Diabetes-induced |
| 4 | 7 | N-Fc-DKK2-Gly4 | 7 µg, twice | Diabetes-induced |
| 5 | 7 | N-Fc-DKK2-Gly4 | 20 µg, twice | Diabetes-induced |
| 6 | 7 | N-Fc-DKK2-Gly4 | 70 µg, twice | Diabetes-induced |

On Day 0 (day of initiation of test material administration), Day 14, and Day 21, a mydriatic (Mydriacyl eye drop 1%) was dropped into the eyes of the rabbits, and anesthetized with Zoletil 50 (VIRBAC, France) and xylazine ((Rompun™), Bayer AG, Germany). Thereafter, a 2% (w/v) fluorescein sodium salt solution (Sigma Aldrich) was injected via the ear vein, and the eyes of the rabbits were photographed using a fundus camera (TRC-50IX, TOPCON, Japan) for about 2 minutes or shorter. Examination of retina and efficacy were evaluated by fluorescent fundus images. Image analysis was performed using ImageJ software (NIH, Bethesda, Md.) to measure fluorescence intensity in non-vascular regions of retina, and based on a mean value (100%) of Group 1 (normal control group), a relative level (%) of the measurement value of each subject was calculated. The calculated fluorescence intensity is shown in FIGS. 3A and 3B (FIG. 3A: Day 14, FIG. 3b: Day 21; * and ***: p<0.05 and p<0.001, respectively, compared to Group 1; #, ##, and ###: p<0.05, p<0.01, and p<0.001, respectively, compared to Group 2; and $: p<0.05, compared to Group 3). As shown in FIGS. 3A and 3B, the N-Fc-DKK2-Gly4-treated group showed significantly low fluorescence intensity in non-vascular regions of retina according to the administration dose, indicating that N-Fc-DKK2-Gly4 has an effect of inhibiting vascular leakage of non-vascular regions of retina.

Further, on Day 21, rabbits were anesthetized with Zoletil 50 and xylazine. A 1% (v/v) Evans blue solution (abcam) was injected via the ear vein. About 10 minutes later, the eyes of the rabbits were excised and fixed in a 10% (v/v) neutral buffered formalin solution. About 24 hours later, the retinas were separated from the eyes, and 1 ml of distilled water was applied to the separated retinas, followed by vortexing for about 10 minutes. The mixture was centrifuged at 10,000×g and room temperature for about 10 minutes. 0.3 ml of the supernatant was transferred to a 96-well microplate and absorbance at 620 nm was measured using a Versa Max Microplate reader (Molecular device, USA). Based on a mean value (100%) of Group 1 (normal control group), Evans blue vascular permeability of each subject was calculated. The calculated permeability is shown in FIG. 4 (* and ***: $p<0.05$ and $p<0.001$, respectively, compared to Group 1; ## and ###: $p<0.01$ and $p<0.001$, respectively, compared to Group 2; and $$: $p<0.01$, compared to Group 3). As shown in FIG. 4, the N-Fc-DKK2-Gly4-treated group showed significantly low vascular permeability according to the administration dose, indicating that N-Fc-DKK2-Gly4 has an effect of inhibiting retinal vascular permeability.

Diabetic retinopathy is characterized by retinal angiogenesis (or neovascularization), vitreous hemorrhage, etc. Since N-Fc-DKK2-Gly4 inhibits angiogenesis, vitreous bleeding, and retinal vascular permeability, the modified DKK2 polypeptide, for example, N-Fc-DKK2-Gly4 was confirmed to have a prophylactic or therapeutic effect on diabetic retinopathy.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A modified Dickkopf-related (DKK)2 polypeptide comprising one or more additional glycosylation sites, compared to an amino acid sequence of a wild-type DKK2 polypeptide.

2. The modified DKK2 polypeptide of claim 1, wherein the wild-type DKK2 polypeptide comprises an amino acid sequence of SEQ ID NO: 3.

3. The modified DKK2 polypeptide of claim 1, wherein the glycosylation is N-glycosylation.

4. The modified DKK2 polypeptide of claim 1, wherein the glycosylation site is Asn-Xaa-Ser/Thr, and Xaa represents any amino acid excluding proline.

5. The modified DKK2 polypeptide of claim 1, wherein the glycosylation site is introduced by substituting asparagine (Asn, N) for one or more amino acids selected form the group consisting of 2L, 5I, 6K, 11G, 31G, 44P, 45C, 57C, 62Q, 63G, 85P, 96P, 98T, 101I, 110D, 121H, 135P, 138K, 151L, 152R, 166F, 187K, 203G, 211D, 213T, and 214Y in an amino acid sequence of SEQ ID NO: 3.

6. The modified DKK2 polypeptide of claim 1, wherein the modified DKK2 polypeptide comprises one or more amino acid sequences selected from the group consisting of SEQ ID NOS: 5 to 30.

7. The modified DKK2 polypeptide of claim 1, further comprising a tag at its N-terminus or C-terminus.

8. The modified DKK2 polypeptide of claim 7, wherein the tag is an Fc (fragment crystallizable) region, a polyhistidine peptide, or a combination thereof.

9. The modified DKK2 polypeptide of claim 1, further comprising a signal peptide at its N-terminus.

10. The modified DKK2 polypeptide of claim 1, wherein the modified DKK2 polypeptide has an addition of glycosyl groups, an increase in binding affinity for low-density lipoprotein receptor-related protein (LRP6), or a combination thereof, compared to the wild-type DKK2 polypeptide.

11. A nucleic acid encoding the modified DKK2 polypeptide of claim 1.

12. The nucleic acid of claim 11, wherein the nucleic acid comprises any one nucleotide sequence selected from the group consisting of SEQ ID NOS: 43 to 47.

13. The nucleic acid of claim 11, further comprising a nucleotide sequence encoding a tag at the 5'-terminus or 3'-terminus of the nucleic acid encoding the modified DKK2 polypeptide.

14. The nucleic acid of claim 11, further comprising a nucleotide sequence encoding a signal peptide at the 5'-terminus of the nucleic acid encoding the modified DKK2 polypeptide.

15. A pharmaceutical composition for promoting angiogenesis, the composition comprising the modified DKK2 polypeptide of claim 1 or the nucleic acid encoding the modified DKK2 polypeptide of claim 1, and a pharmaceutically acceptable carrier.

16. A pharmaceutical composition for preventing or treating vascular permeability-related diseases, the composition comprising the modified DKK2 polypeptide of claim 1 or the nucleic acid encoding the modified DKK2 polypeptide of claim 1, and a pharmaceutically acceptable carrier.

17. A method of preparing the modified DKK2 polypeptide of claim 1, the method comprising:
   culturing cells which are introduced with a vector including a nucleic acid in the presence of a culture medium to obtain a culture product, wherein the nucleic acid is a nucleic acid encoding the modified DKK2 polypeptide of claim 1; and
   obtaining the modified DKK2 polypeptide of claim 1 from the culture product.

18. The method of claim 17, wherein the cell is an embryonic kidney cell, an ovarian cell, a myeloma cell, or a retina-derived cell.

19. A method of promoting angiogenesis of a subject, the method comprising administering the modified DKK2 polypeptide of claim 1 or the nucleic acid encoding the modified DKK2 polypeptide of claim 1 to the subject.

20. A method of preventing or treating a vascular permeability-related disease of a subject, the method comprising administering the modified DKK2 polypeptide of claim 1 or the nucleic acid encoding the modified DKK2 polypeptide of claim 1 to the subject.

* * * * *

SEQUENCE LISTING

<160> NUMBER OF SEQ ID NOS: 49

<210> SEQ ID NO 1
<211> LENGTH: 259
<212> TYPE: PRT
<213> ORGANISM: Artificial Sequence
<220> FEATURE:
<223> OTHER INFORMATION: Human wildtype DKK2 precursor

<400> SEQUENCE: 1

Met Ala Ala Leu Met Arg Ser Lys Asp Ser Ser Cys Cys Leu Leu Leu
 1               5                  10                  15

Leu Ala Ala Val Leu Met Val Glu Ser Ser Gln Ile Gly Ser Ser Arg
            20                  25                  30

Ala Lys Leu Asn Ser Ile Lys Ser Ser Leu Gly Gly Glu Thr Pro Gly
        35                  40                  45

Gln Ala Ala Asn Arg Ser Ala Gly Met Tyr Gln Gly Leu Ala Phe Gly
    50                  55                  60

Gly Ser Lys Lys Gly Lys Asn Leu Gly Gln Ala Tyr Pro Cys Ser Ser
65                  70                  75                  80

Asp Lys Glu Cys Glu Val Gly Arg Tyr Cys His Ser Pro His Gln Gly
                85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
    130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
            180                 185                 190

Phe Cys Cys Ala Arg His Phe Trp Thr Lys Ile Cys Lys Pro Val Leu
        195                 200                 205

His Gln Gly Glu Val Cys Thr Lys Gln Arg Lys Lys Gly Ser His Gly
    210                 215                 220

```
Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile
```

<210> SEQ ID NO 2
<211> LENGTH: 33
<212> TYPE: PRT
<213> ORGANISM: Artificial Sequence
<220> FEATURE:
<223> OTHER INFORMATION: Signal peptide of human wildtype DKK2

<400> SEQUENCE: 2

```
Met Ala Ala Leu Met Arg Ser Lys Asp Ser Ser Cys Cys Leu Leu Leu
1               5                   10                  15

Leu Ala Ala Val Leu Met Val Glu Ser Ser Gln Ile Gly Ser Ser Arg
            20                  25                  30

Ala
```

<210> SEQ ID NO 3
<211> LENGTH: 226
<212> TYPE: PRT
<213> ORGANISM: Artificial Sequence
<220> FEATURE:
<223> OTHER INFORMATION: Human wildtype mature DKK2

<400> SEQUENCE: 3

```
Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220
```

Lys Ile
225

<210> SEQ ID NO 4
<211> LENGTH: 3659
<212> TYPE: DNA
<213> ORGANISM: Artificial Sequence
<220> FEATURE:
<223> OTHER INFORMATION: Human DKK2 mRNA

<400> SEQUENCE: 4

```
cgggagcccg cggcgagcgt agcgcaagtc cgctccctag gcatcgctgc gctggcagcg      60
attcgctgtc tcttgtgagt caggggacaa cgcttcgggg caactgtgag tgcgcgtgtg     120
ggggacctcg attctcttca gatctcgagg attcggtccg gggacgtctc ctgatcccct     180
actaaagcgc ctgctaactt tgaaaaggag cactgtgtcc tgcaaagttt gacacataaa     240
ggataggaaa agagaggaga gaaaagcaac tgagttgaag gagaaggagc tgatgcgggc     300
ctcctgatca attaagagga gagttaaacc gccgagatcc cggcgggacc aaggaggtgc     360
ggggcaagaa ggaacggaag cggtgcgatc acagggctg gttttcttg caccttgggt       420
cacgcctcct tggcgagaaa gcgcctcgca tttgattgct ccagttatt gcagaacttc      480
ctgtcctggt ggagaagcgg gtctcgcttg gttccgcta atttctgtcc tgaggcgtga      540
gactgagttc atagggtcct gggtccccga accaggaagg gttgagggaa cacaatctgc     600
aagcccccgc gacccaagtg aggggccccg tgttggggtc ctccctccct ttgcattccc     660
accctccgg gctttgcgtc ttcctgggga cccctcgcc gggagatggc cgcgttgatg       720
cggagcaagg attcgtcctg ctgcctgctc ctactggccg cggtgctgat ggtggagagc     780
tcacagatcg gcagttcgcg ggccaaactc aactccatca gtcctctct gggcggggag      840
acgcctggtc aggccgccaa tcgatctgcg ggcatgtacc aaggactggc attcggcggc    900
agtaagaagg gcaaaaacct ggggcaggcc taccttgta gcagtgataa ggagtgtgaa      960
gttgggaggt attgccacag tccccaccaa ggatcatcgg cctgcatggt gtgtcggaga    1020
aaaaagaagc gctgccaccg agatggcatg tgctgcccca gtacccgctg caataatggc    1080
atctgtatcc cagttactga aagcatctta accctcaca tcccggctct ggatggtact     1140
cggcacagag atcgaaacca cggtcattac tcaaaccatg acttgggatg cagaatcta    1200
ggaagaccac acactaagat gtcacatata aagggcatg aaggagaccc ctgcctacga    1260
tcatcagact gcattgaagg ttttgctgt gctcgtcatt tctggaccaa aatctgcaaa    1320
ccagtgctcc atcaggggga agtctgtacc aaacaacgca agaagggttc tcatgggctg    1380
gaaattttcc agcgttgcga ctgtgcgaag ggcctgtctt gcaaagtatg aaagatgcc    1440
acctactcct ccaaagccag actccatgtg tgtcagaaaa tttgatcacc attgaggaac    1500
atcatcaatt gcagactgtg aagttgtgta tttaatgcat tatagcatgg tggaaaataa    1560
ggttcagatg cagaagaatg gctaaaataa gaaacgtgat aagaatatag atgatcacaa    1620
aaagggagaa agaaaacatg aactgaatag attagaatgg gtgacaaatg cagtgcagcc    1680
agtgttttcca ttatgcaact tgtctatgta aataatgtac acatttgtgg aaaatgctat    1740
tattaagaga acaagcacac agtggaaatt actgatgagt agcatgtgac tttccaagag    1800
tttaggttgt gctggaggag aggtttcctt cagattgctg attgcttata caaataacct    1860
acatgccaga tttctattca acgttagagt ttaacaaaat actccctagaa taacttgtta   1920
tacaataggt tctaaaaata aaattgctaa acaagaaatg aaaacatgga gcattgttaa    1980
```

```
tttacaacag aaaattacct tttgatttgt aacactactt ctgctgttca atcaagagtc    2040
ttggtagata agaaaaaaat cagtcaatat ttccaaataa ttgcaaaata atggccagtt    2100
gtttaggaag cctttagga agacaaataa ataacaaaca aacagccaca aatactttt     2160 tttcaaaatt ttagttttac ctgtaattaa taagaactga tacaagacaa aaacagttcc    2220
ttcagattct acggaatgac agtatatctc tctttatcct atgtgattcc tgctctgaat    2280
gcattatatt ttccaaacta tacccataaa ttgtgactag taaaatactt acacagagca    2340
gaattttcac agatggcaaa aaaatttaaa gatgtccaat atatgtggga aaagagctaa    2400
cagagagatc attatttctt aaagattggc ataacctgt attttgatag aattagattg     2460
gtaaatacat gtattcatac atactctgtg gtaatagaga cttgagctgg atctgtactg    2520
cactggagta agcaagaaaa ttgggaaaac ttttcgttt gttcaggttt tggcaacaca     2580
tagatcatat gtctgaggca caagttggct gttcatcttt gaaaccaggg gatgcacagt    2640
ctaaatgaat atctgcatgg gatttgctat cataatattt actatgcaga tgaattcagt    2700
gtgaggtcct gtgtccgtac tatcctcaaa ttatttattt tatagtgctg agatcctcaa    2760
ataatctcaa tttcaggagg tttcacaaaa tggactcctg aagtagacag agtagtgagg    2820
tttcattgcc ctctataagc ttctgactag ccaatggcat catccaattt tcttcccaaa    2880
cctctgcagc atctgcttta ttgccaaagg gctagtttcg gttttctgca gccattgcgg    2940
ttaaaaaata taagtaggat aacttgtaaa acctgcatat tgctaatcta tagacaccac    3000
agtttctaaa ttctttgaaa ccactttact acttttttta aacttaactc agttctaaat    3060
actttgtctg gagcacaaaa caataaaagg ttatcttata gtcgtgactt taaaactttg    3120
tagaccacaa ttcactttt agttttcttt tacttaaatc ccatctgcag tctcaaattt     3180
aagttctccc agtagagatt gagtttgagc ctgtatatct attaaaaatt tcaacttccc    3240
acatatattt actaagatga ttaagactta cattttctgc acaggtctgc aaaaacaaaa    3300
attataaact agtccatcca agaaccaaag tttgtataaa caggttgcta taagcttggt    3360
gaaatgaaaa tggaacattt caatcaaaca tttcctatat aacaattatt atatttacaa    3420 tttggttct gcaatatttt tcttatgtcc accctttaa aaattattat ttgaagtaat      3480
ttatttacag gaaatgttaa tgagatgtat tttcttatag agatatttct tacagaaagc    3540
tttgtagcag aatatatttg cagctattga ctttgtaatt taggaaaaat gtataataag    3600
ataaaatcta ttaatttttt ctcctctaaa aactgaaaaa aaaaaaaaaa aaaaaaaa      3659
```

<210> SEQ ID NO 5
<211> LENGTH: 226
<212> TYPE: PRT
<213> ORGANISM: Artificial Sequence
<220> FEATURE:
<223> OTHER INFORMATION: DKK2 N-Gly1

<400> SEQUENCE: 5

Lys Leu Asn Ser Asn Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Lys Arg Cys His Arg Asp

```
                65                  70                  75                  80
Gly Met Cys Cys Pro Ser Thr Arg Cys Asn Asn Gly Ile Cys Ile Pro
                    85                  90                  95

Val Thr Glu Ser Ile Leu Thr Pro His Ile Pro Ala Leu Asp Gly Thr
                100                 105                 110

Arg His Arg Asp Arg Asn His Gly His Tyr Ser Asn His Asp Leu Gly
                115                 120                 125

Trp Gln Asn Leu Gly Arg Pro His Thr Lys Met Ser His Ile Lys Gly
                130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
                180                 185                 190

Glu Ile Phe Gln Arg Cys Asp Cys Ala Lys Gly Leu Ser Cys Lys Val
                195                 200                 205

Trp Lys Asp Ala Thr Tyr Ser Ser Lys Ala Arg Leu His Val Cys Gln
210                 215                 220

Lys Ile
225

<210> SEQ ID NO 6
<211> LENGTH: 226
<212> TYPE: PRT
<213> ORGANISM: Artificial Sequence
<220> FEATURE:
<223> OTHER INFORMATION: DKK2 N-Gly2

<400> SEQUENCE: 6

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Asn Gly
                20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                    85                  90                  95

Val Thr Glu Ser Ile Leu Thr Pro His Ile Pro Ala Leu Asp Gly Thr
                100                 105                 110

Arg His Arg Asp Arg Asn His Gly His Tyr Ser Asn His Asp Leu Gly
                115                 120                 125

Trp Gln Asn Leu Gly Arg Pro His Thr Lys Met Ser His Ile Lys Gly
                130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
                180                 185                 190

Glu Ile Phe Gln Arg Cys Asp Cys Ala Lys Gly Leu Ser Cys Lys Val
```

```
                195                 200                 205

Trp Lys Asp Ala Thr Tyr Ser Ser Lys Ala Arg Leu His Val Cys Gln
    210                 215                 220

Lys Ile
225

<210> SEQ ID NO 7
<211> LENGTH: 226
<212> TYPE: PRT
<213> ORGANISM: Artificial Sequence
<220> FEATURE:
<223> OTHER INFORMATION: DKK2 N-Gly3

<400> SEQUENCE: 7

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Cys Ser Ser Asp
         35                  40                  45

Lys Glu Cys Glu Val Gly Arg Tyr Cys His Ser Pro His Gln Gly Ser
 50                  55                  60

Ser Ala Cys Met Val Cys Arg Lys Lys Arg Cys His Arg Asp
 65                  70                  75                  80

Gly Met Cys Cys Pro Ser Thr Arg Cys Asn Asn Gly Ile Cys Ile Asn
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 8
<211> LENGTH: 226
<212> TYPE: PRT
<213> ORGANISM: Artificial Sequence
<220> FEATURE:
<223> OTHER INFORMATION: DKK2 N-Gly4

<400> SEQUENCE: 8

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30
```

```
Ser Lys Lys Gly Lys Asn Leu Gly Gln Ala Tyr Pro Cys Ser Ser Asp
         35                  40                  45

Lys Glu Cys Glu Val Gly Arg Tyr Cys His Ser Pro His Gln Gly Ser
 50                  55                  60

Ser Ala Cys Met Val Cys Arg Lys Lys Arg Cys His Arg Asp
 65                  70                  75                  80

Gly Met Cys Cys Pro Ser Thr Arg Cys Asn Asn Gly Ile Cys Ile Pro
                     85                  90                  95

Val Thr Glu Ser Ile Leu Thr Pro His Ile Pro Ala Leu Asn Gly Thr
                 100                 105                 110

Arg His Arg Asp Arg Asn His Gly His Tyr Ser Asn His Asp Leu Gly
                 115                 120                 125

Trp Gln Asn Leu Gly Arg Pro His Thr Lys Met Ser His Ile Lys Gly
 130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                 165                 170                 175

Gln Gly Glu Val Cys Thr Lys Gln Arg Lys Lys Gly Ser His Gly Leu
                 180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
            210                 215                 220

Lys Ile
225

<210> SEQ ID NO 9
<211> LENGTH: 226
<212> TYPE: PRT
<213> ORGANISM: Artificial Sequence
<220> FEATURE:
<223> OTHER INFORMATION: DKK2 N-Gly5

<400> SEQUENCE: 9

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
                 20                  25                  30

Ser Lys Lys Gly Lys Asn Leu Gly Gln Ala Tyr Asn Cys Ser Ser Asp
         35                  40                  45

Lys Glu Cys Glu Val Gly Arg Tyr Cys His Ser Pro His Gln Gly Ser
 50                  55                  60

Ser Ala Cys Met Val Cys Arg Lys Lys Arg Cys His Arg Asp
 65                  70                  75                  80

Gly Met Cys Cys Pro Ser Thr Arg Cys Asn Asn Gly Ile Cys Ile Pro
                     85                  90                  95

Val Thr Glu Ser Ile Leu Thr Pro His Ile Pro Ala Leu Asp Gly Thr
                 100                 105                 110

Arg His Arg Asp Arg Asn His Gly His Tyr Ser Asn His Asp Leu Gly
                 115                 120                 125

Trp Gln Asn Leu Gly Arg Pro His Thr Lys Met Ser His Ile Lys Gly
 130                 135                 140

His Glu Gly Asp Pro Cys Leu Arg Ser Ser Asp Cys Ile Glu Gly Phe
145                 150                 155                 160
```

```
Cys Cys Ala Arg His Phe Trp Thr Lys Ile Cys Lys Pro Val Leu His
            165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
210                 215                 220

Lys Ile
225

<210> SEQ ID NO 10
<211> LENGTH: 226
<212> TYPE: PRT
<213> ORGANISM: Artificial Sequence
<220> FEATURE:
<223> OTHER INFORMATION: DKK2 N-Gly6

<400> SEQUENCE: 10

Lys Asn Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
50                  55                  60

Ser Ala Cys Met Val Cys Arg Arg Lys Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
            130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
            165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
210                 215                 220

Lys Ile
225

<210> SEQ ID NO 11
<211> LENGTH: 226
<212> TYPE: PRT
<213> ORGANISM: Artificial Sequence
<220> FEATURE:
<223> OTHER INFORMATION: DKK2 N-Gly7

<400> SEQUENCE: 11
```

```
Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Asn Ser Ser Asp
         35                  40                  45

Lys Glu Cys Glu Val Gly Arg Tyr Cys His Ser Pro His Gln Gly Ser
     50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
            130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
    210                 215                 220

Lys Ile
225

<210> SEQ ID NO 12
<211> LENGTH: 226
<212> TYPE: PRT
<213> ORGANISM: Artificial Sequence
<220> FEATURE:
<223> OTHER INFORMATION: DKK2 N-Gly8

<400> SEQUENCE: 12

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Cys Ser Ser Asp
         35                  40                  45

Lys Glu Cys Glu Val Gly Arg Tyr Asn His Ser Pro His Gln Gly Ser
     50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
            115                 120                 125
```

```
Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 13
<211> LENGTH: 226
<212> TYPE: PRT
<213> ORGANISM: Artificial Sequence
<220> FEATURE:
<223> OTHER INFORMATION: DKK2 N-Gly9

<400> SEQUENCE: 13

Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Asn Gly Ser
    50                  55                  60

Ser Ala Cys Met Val Cys Arg Arg Lys Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 14
```

<211> LENGTH: 226
<212> TYPE: PRT
<213> ORGANISM: Artificial Sequence
<220> FEATURE:
<223> OTHER INFORMATION: DKK2 N-Gly10

<400> SEQUENCE: 14

Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Asn Ser
    50                  55                  60

Ser Ala Cys Met Val Cys Arg Arg Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 15
<211> LENGTH: 226
<212> TYPE: PRT
<213> ORGANISM: Artificial Sequence
<220> FEATURE:
<223> OTHER INFORMATION: DKK2 N-Gly11

<400> SEQUENCE: 15

Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Arg Cys His Arg Asp
65                  70                  75                  80

Gly Met Cys Cys Asn Ser Thr Arg Cys Asn Asn Gly Ile Cys Ile Pro

```
                    85                  90                  95
Val Thr Glu Ser Ile Leu Thr Pro His Ile Pro Ala Leu Asp Gly Thr
                100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
        130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 16
<211> LENGTH: 226
<212> TYPE: PRT
<213> ORGANISM: Artificial Sequence
<220> FEATURE:
<223> OTHER INFORMATION: DKK2 N-Gly12

<400> SEQUENCE: 16

Lys Leu Asn Ser Ile Asn Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
                20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
                100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
        130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
```

<210> SEQ ID NO 17
<211> LENGTH: 226
<212> TYPE: PRT
<213> ORGANISM: Artificial Sequence
<220> FEATURE:
<223> OTHER INFORMATION: DKK2 N-Gly13

<400> SEQUENCE: 17

```
Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Cys Ser Ser Asp
         35                  40                  45

Lys Glu Cys Glu Val Gly Arg Tyr Cys His Ser Pro His Gln Gly Ser
 50                  55                  60

Ser Ala Cys Met Val Cys Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Asn Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
210                 215                 220

Lys Ile
225
```

<210> SEQ ID NO 18
<211> LENGTH: 226
<212> TYPE: PRT
<213> ORGANISM: Artificial Sequence
<220> FEATURE:
<223> OTHER INFORMATION: DKK2 N-Gly14

<400> SEQUENCE: 18

```
Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Cys Ser Ser Asp
         35                  40                  45
```

```
Lys Glu Cys Glu Val Gly Arg Tyr Cys His Ser Pro His Gln Gly Ser
 50                  55                  60
Ser Ala Cys Met Val Cys Arg Arg Lys Lys Arg Cys His Arg Asp
 65                  70                  75                  80
Gly Met Cys Cys Pro Ser Thr Arg Cys Asn Asn Gly Ile Cys Ile Pro
                 85                  90                  95
Val Thr Glu Ser Asn Leu Thr Pro His Ile Pro Ala Leu Asp Gly Thr
                100                 105                 110
Arg His Arg Asp Arg Asn His Gly His Tyr Ser Asn His Asp Leu Gly
                115                 120                 125
Trp Gln Asn Leu Gly Arg Pro His Thr Lys Met Ser His Ile Lys Gly
130                 135                 140
His Glu Gly Asp Pro Cys Leu Arg Ser Ser Asp Cys Ile Glu Gly Phe
145                 150                 155                 160
Cys Cys Ala Arg His Phe Trp Thr Lys Ile Cys Lys Pro Val Leu His
                165                 170                 175
Gln Gly Glu Val Cys Thr Lys Arg Lys Lys Gly Ser His Gly Leu
                180                 185                 190
Glu Ile Phe Gln Arg Cys Asp Cys Ala Lys Gly Leu Ser Cys Lys Val
                195                 200                 205
Trp Lys Asp Ala Thr Tyr Ser Ser Lys Ala Arg Leu His Val Cys Gln
210                 215                 220
Lys Ile
225

<210> SEQ ID NO 19
<211> LENGTH: 226
<212> TYPE: PRT
<213> ORGANISM: Artificial Sequence
<220> FEATURE:
<223> OTHER INFORMATION: DKK2 N-Gly15

<400> SEQUENCE: 19

Lys Leu Asn Ser Ile Lys Ser Ser Leu Gly Asn Glu Thr Pro Gly Gln
  1               5                  10                  15
Ala Ala Asn Arg Ser Ala Gly Met Tyr Gln Gly Leu Ala Phe Gly Gly
                 20                  25                  30
Ser Lys Lys Gly Lys Asn Leu Gly Gln Ala Tyr Pro Cys Ser Ser Asp
                 35                  40                  45
Lys Glu Cys Glu Val Gly Arg Tyr Cys His Ser Pro His Gln Gly Ser
 50                  55                  60
Ser Ala Cys Met Val Cys Arg Arg Lys Lys Arg Cys His Arg Asp
 65                  70                  75                  80
Gly Met Cys Cys Pro Ser Thr Arg Cys Asn Asn Gly Ile Cys Ile Pro
                 85                  90                  95
Val Thr Glu Ser Ile Leu Thr Pro His Ile Pro Ala Leu Asp Gly Thr
                100                 105                 110
Arg His Arg Asp Arg Asn His Gly His Tyr Ser Asn His Asp Leu Gly
                115                 120                 125
Trp Gln Asn Leu Gly Arg Pro His Thr Lys Met Ser His Ile Lys Gly
130                 135                 140
His Glu Gly Asp Pro Cys Leu Arg Ser Ser Asp Cys Ile Glu Gly Phe
145                 150                 155                 160
Cys Cys Ala Arg His Phe Trp Thr Lys Ile Cys Lys Pro Val Leu His
                165                 170                 175
```

```
Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 20
<211> LENGTH: 226
<212> TYPE: PRT
<213> ORGANISM: Artificial Sequence
<220> FEATURE:
<223> OTHER INFORMATION: DKK2 N-Gly16

<400> SEQUENCE: 20

Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly Asn Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 21
<211> LENGTH: 226
<212> TYPE: PRT
<213> ORGANISM: Artificial Sequence
<220> FEATURE:
<223> OTHER INFORMATION: DKK2 N-Gly17

<400> SEQUENCE: 21

Lys Leu Asn Ser Ile Lys Ser Ser Leu Gly Gly Glu Thr Pro Gly Gln
1               5                   10                  15
```

-continued

```
Ala Ala Asn Arg Ser Ala Gly Met Tyr Gln Gly Leu Ala Phe Gly Gly
         20                  25                  30

Ser Lys Lys Gly Lys Asn Leu Gly Gln Ala Tyr Pro Cys Ser Ser Asp
     35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
             100                 105                 110

Arg His Arg Asp Arg Asn His Gly His Tyr Ser Asn His Asp Leu Gly
         115                 120                 125

Trp Gln Asn Leu Gly Arg Asn His Thr Lys Met Ser His Ile Lys Gly
130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                 165                 170                 175

Gln Gly Glu Val Cys Thr Lys Gln Arg Lys Lys Gly Ser His Gly Leu
             180                 185                 190

Glu Ile Phe Gln Arg Cys Asp Cys Ala Lys Gly Leu Ser Cys Lys Val
         195                 200                 205

Trp Lys Asp Ala Thr Tyr Ser Ser Lys Ala Arg Leu His Val Cys Gln
210                 215                 220

Lys Ile
225

<210> SEQ ID NO 22
<211> LENGTH: 226
<212> TYPE: PRT
<213> ORGANISM: Artificial Sequence
<220> FEATURE:
<223> OTHER INFORMATION: DKK2 N-Gly18

<400> SEQUENCE: 22

Lys Leu Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
         20                  25                  30

Ser Lys Lys Gly Lys Asn Leu Gly Gln Ala Tyr Pro Cys Ser Ser Asp
     35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
             100                 105                 110

Arg His Arg Asp Arg Asn His Gly His Tyr Ser Asn His Asp Leu Gly
         115                 120                 125

Trp Gln Asn Leu Gly Arg Pro His Thr Asn Met Ser His Ile Lys Gly
130                 135                 140
```

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 23
<211> LENGTH: 226
<212> TYPE: PRT
<213> ORGANISM: Artificial Sequence
<220> FEATURE:
<223> OTHER INFORMATION: DKK2 N-Gly19

<400> SEQUENCE: 23

Lys Leu Asn Ser Ile Lys Ser Ser Leu Gly Gly Glu Thr Pro Gly Gln
1               5                   10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Asn Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 24
<211> LENGTH: 226
<212> TYPE: PRT
<213> ORGANISM: Artificial Sequence

```
<220> FEATURE:
<223> OTHER INFORMATION: DKK2 N-Gly20

<400> SEQUENCE: 24

Lys Leu Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
                20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
50                  55                  60

Ser Ala Cys Met Val Cys Arg Arg Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
130                 135                 140

His Glu Gly Asp Pro Cys Leu Asn Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asp Ala Thr Tyr Ser Ser Lys Ala Arg Leu His Val Cys Gln
210                 215                 220

Lys Ile
225

<210> SEQ ID NO 25
<211> LENGTH: 226
<212> TYPE: PRT
<213> ORGANISM: Artificial Sequence
<220> FEATURE:
<223> OTHER INFORMATION: DKK2 N-Gly21

<400> SEQUENCE: 25

Lys Leu Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
                20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
50                  55                  60

Ser Ala Cys Met Val Cys Arg Arg Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
```

```
            100                 105                 110
Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
            130                 135                 140

His Glu Gly Asp Pro Cys Leu Arg Ser Ser Asp Cys Ile Glu Gly Phe
145                 150                 155                 160

Cys Cys Ala Arg His Asn Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
            210                 215                 220

Lys Ile
225
```

<210> SEQ ID NO 26
<211> LENGTH: 226
<212> TYPE: PRT
<213> ORGANISM: Artificial Sequence
<220> FEATURE:
<223> OTHER INFORMATION: DKK2 N-Gly22

<400> SEQUENCE: 26

```
Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
                20                  25                  30

Ser Lys Lys Gly Lys Asn Leu Gly Gln Ala Tyr Pro Cys Ser Ser Asp
            35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Lys Arg Cys His Arg Asp
 65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
            130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Asn Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Tyr Ser Ser Lys Ala Arg Leu His Val Cys Gln
            210                 215                 220

Lys Ile
```

-continued

225

<210> SEQ ID NO 27
<211> LENGTH: 226
<212> TYPE: PRT
<213> ORGANISM: Artificial Sequence
<220> FEATURE:
<223> OTHER INFORMATION: DKK2 N-Gly23

<400> SEQUENCE: 27

Lys Leu Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

Ser Ala Cys Met Val Cys Arg Arg Lys Lys Arg Cys His Arg Asp
65                  70                  75                  80

Gly Met Cys Cys Pro Ser Thr Arg Cys Asn Asn Gly Ile Cys Ile Pro
                85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
        115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Asn Leu Ser Cys Lys Val
        195                 200                 205

Trp Lys Asp Ala Thr Tyr Ser Ser Lys Ala Arg Leu His Val Cys Gln
    210                 215                 220

Lys Ile
225

<210> SEQ ID NO 28
<211> LENGTH: 226
<212> TYPE: PRT
<213> ORGANISM: Artificial Sequence
<220> FEATURE:
<223> OTHER INFORMATION: DKK2 N-Gly24

<400> SEQUENCE: 28

Lys Leu Asn Ser Ile Lys Ser Ser Leu Gly Gly Glu Thr Pro Gly Gln
 1               5                  10                  15

Ala Ala Asn Arg Ser Ala Gly Met Tyr Gln Gly Leu Ala Phe Gly Gly
            20                  25                  30

Ser Lys Lys Gly Lys Asn Leu Gly Gln Ala Tyr Pro Cys Ser Ser Asp
        35                  40                  45

Lys Glu Cys Glu Val Gly Arg Tyr Cys His Ser Pro His Gln Gly Ser
    50                  55                  60

```
Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
                115                 120                 125

Trp Gln Asn Leu Gly Arg Pro His Thr Lys Met Ser His Ile Lys Gly
        130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
        195                 200                 205

Trp Lys Asn Ala Thr Tyr Ser Ser Lys Ala Arg Leu His Val Cys Gln
    210                 215                 220

Lys Ile
225

<210> SEQ ID NO 29
<211> LENGTH: 226
<212> TYPE: PRT
<213> ORGANISM: Artificial Sequence
<220> FEATURE:
<223> OTHER INFORMATION: DKK2 N-Gly25

<400> SEQUENCE: 29

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
                 20                  25                  30

Ser Lys Lys Gly Lys Asn Leu Gly Gln Ala Tyr Pro Cys Ser Ser Asp
             35                  40                  45

Lys Glu Cys Glu Val Gly Arg Tyr Cys His Ser Pro His Gln Gly Ser
         50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
                115                 120                 125

Trp Gln Asn Leu Gly Arg Pro His Thr Lys Met Ser His Ile Lys Gly
        130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190
```

```
Glu Ile Phe Gln Arg Cys Asp Cys Ala Lys Gly Leu Ser Cys Lys Val
            195                 200                 205

Trp Lys Asp Ala Asn Tyr Ser Ser Lys Ala Arg Leu His Val Cys Gln
    210                 215                 220

Lys Ile
225

<210> SEQ ID NO 30
<211> LENGTH: 226
<212> TYPE: PRT
<213> ORGANISM: Artificial Sequence
<220> FEATURE:
<223> OTHER INFORMATION: DKK2 N-Gly26

<400> SEQUENCE: 30

Lys Leu Asn Ser Ile Lys Ser Ser Leu Gly Gly Glu Thr Pro Gly Gln
  1               5                  10                  15

Ala Ala Asn Arg Ser Ala Gly Met Tyr Gln Gly Leu Ala Phe Gly Gly
             20                  25                  30

Ser Lys Lys Gly Lys Asn Leu Gly Gln Ala Tyr Pro Cys Ser Ser Asp
         35                  40                  45

Lys Glu Cys Glu Val Gly Arg Tyr Cys His Ser Pro His Gln Gly Ser
 50                  55                  60

Ser Ala Cys Met Val Cys Arg Arg Lys Lys Arg Cys His Arg Asp
 65                  70                  75                  80

Gly Met Cys Cys Pro Ser Thr Arg Cys Asn Asn Gly Ile Cys Ile Pro
                 85                  90                  95

Val Thr Glu Ser Ile Leu Thr Pro His Ile Pro Ala Leu Asp Gly Thr
            100                 105                 110

Arg His Arg Asp Arg Asn His Gly His Tyr Ser Asn His Asp Leu Gly
            115                 120                 125

Trp Gln Asn Leu Gly Arg Pro His Thr Lys Met Ser His Ile Lys Gly
    130                 135                 140

His Glu Gly Asp Pro Cys Leu Arg Ser Ser Asp Cys Ile Glu Gly Phe
145                 150                 155                 160

Cys Cys Ala Arg His Phe Trp Thr Lys Ile Cys Lys Pro Val Leu His
                165                 170                 175

Gln Gly Glu Val Cys Thr Lys Gln Arg Lys Lys Gly Ser His Gly Leu
            180                 185                 190

Glu Ile Phe Gln Arg Cys Asp Cys Ala Lys Gly Leu Ser Cys Lys Val
            195                 200                 205

Trp Lys Asp Ala Thr Asn Ser Ser Lys Ala Arg Leu His Val Cys Gln
    210                 215                 220

Lys Ile
225

<210> SEQ ID NO 31
<211> LENGTH: 40
<212> TYPE: DNA
<213> ORGANISM: Artificial Sequence
<220> FEATURE:
<223> OTHER INFORMATION: Forward primer for DKK2 N-Gly1

<400> SEQUENCE: 31
ggcatgtgct gcaacagtac ccgctgcaat aatggcatct                          40

<210> SEQ ID NO 32
<211> LENGTH: 38
```

```
<212> TYPE: DNA
<213> ORGANISM: Artificial Sequence
<220> FEATURE:
<223> OTHER INFORMATION: Reverse primer for DKK2 N-Gly1

<400> SEQUENCE: 32
gcagcgggta ctgttgcagc acatgccatc tcggtggc                              38

<210> SEQ ID NO 33
<211> LENGTH: 42
<212> TYPE: DNA
<213> ORGANISM: Artificial Sequence
<220> FEATURE:
<223> OTHER INFORMATION: Forward primer for DKK2 N-Gly2

<400> SEQUENCE: 33
aatctaggaa gaaatcacac taagatgtca catataaaag gg                          42

<210> SEQ ID NO 34
<211> LENGTH: 42
<212> TYPE: DNA
<213> ORGANISM: Artificial Sequence
<220> FEATURE:
<223> OTHER INFORMATION: Reverse primer for DKK2 N-Gly2

<400> SEQUENCE: 34
catcttagtg tgatttcttc ctagattctg ccatcccaag tc                          42

<210> SEQ ID NO 35
<211> LENGTH: 41
<212> TYPE: DNA
<213> ORGANISM: Artificial Sequence
<220> FEATURE:
<223> OTHER INFORMATION: Forward primer for DKK2 N-Gly3

<400> SEQUENCE: 35
catcaggggg aaaactgtac caaacaacgc aagaagggtt c                           41

<210> SEQ ID NO 36
<211> LENGTH: 40
<212> TYPE: DNA
<213> ORGANISM: Artificial Sequence
<220> FEATURE:
<223> OTHER INFORMATION: Reverse primer for DKK2 N-Gly3

<400> SEQUENCE: 36
ttgtttggta cagttttccc cctgatggag cactggtttg                             40

<210> SEQ ID NO 37
<211> LENGTH: 39
<212> TYPE: DNA
<213> ORGANISM: Artificial Sequence
<220> FEATURE:
<223> OTHER INFORMATION: Forward primer for DKK2 N-Gly3

<400> SEQUENCE: 37
atcccggctc tgaatggtac tcggcacaga gatcgaaac                              39

<210> SEQ ID NO 38
<211> LENGTH: 39
<212> TYPE: DNA
<213> ORGANISM: Artificial Sequence
<220> FEATURE:
<223> OTHER INFORMATION: Reverse primer for DKK2 N-Gly4

<400> SEQUENCE: 38
```

-continued gtgccgagta ccattcagag ccgggatgtg aggggttaa                          39

<210> SEQ ID NO 39
<211> LENGTH: 42
<212> TYPE: DNA
<213> ORGANISM: Artificial Sequence
<220> FEATURE:
<223> OTHER INFORMATION: Forward primer for DKK2 N-Gly5

<400> SEQUENCE: 39
gggcaggcct acaattgtag cagtgataag gagtgtgaag tt                      42

<210> SEQ ID NO 40
<211> LENGTH: 39
<212> TYPE: DNA
<213> ORGANISM: Artificial Sequence
<220> FEATURE:
<223> OTHER INFORMATION: Reverse primer for DKK2 N-Gly5

<400> SEQUENCE: 40
atcactgcta caattgtagg cctgccccag gttttttgcc                         39

<210> SEQ ID NO 41
<211> LENGTH: 29
<212> TYPE: DNA
<213> ORGANISM: Artificial Sequence
<220> FEATURE:
<223> OTHER INFORMATION: Forward primer for vector

<400> SEQUENCE: 41
accggtggta ccgccaccat gggatggag                                     29

<210> SEQ ID NO 42
<211> LENGTH: 29
<212> TYPE: DNA
<213> ORGANISM: Artificial Sequence
<220> FEATURE:
<223> OTHER INFORMATION: Reverse primer for vector

<400> SEQUENCE: 42
ggatttatac aaggaggaga aaatgaaag                                     29

<210> SEQ ID NO 43
<211> LENGTH: 678
<212> TYPE: DNA
<213> ORGANISM: Artificial Sequence
<220> FEATURE:
<223> OTHER INFORMATION: Nucleic acid encoding DKK2 N-Gly1 polypeptide

<400> SEQUENCE: 43
aaactcaact ccaacaagtc ctctctgggc ggggagacgc tggtcaggc cgccaatcga     60 tctgcgggca tgtaccaagg actggcattc ggcggcagta agaagggcaa aaacctgggg    120
caggcctacc cttgtagcag tgataaggag tgtgaagttg gaggtattg ccacagtccc     180 caccaaggat catcggcctg catggtgtgt cggagaaaaa agaagcgctg ccaccgagat    240
ggcatgtgct gccccagtac ccgctgcaat aatggcatct gtatcccagt tactgaaagc    300
atcttaaccc ctcacatccc ggctctggat ggtactcggc acagagatcg aaaccacggt    360
cattactcaa accatgactt gggatggcag aatctaggaa gaccacacac taagatgtca    420
catataaaag gcatgaagg agaccctgc ctacgatcat cagactgcat tgaagggttt      480
tgctgtgctc gtcatttctg gaccaaaatc tgcaaaccag tgctccatca ggggaagtc     540 tgtaccaaac aacgcaagaa gggttctcat ggctggaaaa ttttccagcg ttgcgactgt    600
gcgaagggcc tgtcttgcaa agtatggaaa gatgccacct actcctccaa agccagactc    660
catgtgtgtc agaaaatt                                                  678

<210> SEQ ID NO 44
<211> LENGTH: 681
<212> TYPE: DNA
<213> ORGANISM: Artificial Sequence
<220> FEATURE:
<223> OTHER INFORMATION: Nucleic acid encoding DKK2 N-Gly2 polypeptide

<400> SEQUENCE: 44
aaactcaact ccatcaagtc ctctctgggc ggggagacgc ctggtcaggc cgccaatcga     60
tctgcgggca tgtaccaagg actggcattc aatggcagta agaagggcaa aaacctgggg    120
caggcctacc cttgtagcag tgataaggag tgtgaagttg ggaggtattg ccacagtccc    180
caccaaggat catcggcctg catggtgtgt cggagaaaaa agaagcgctg ccaccgagat    240
ggcatgtgct gccccagtac ccgctgcaat aatggcatct gtatcccagt tactgaaagc    300
atcttaaccc ctcacatccc ggctctggat ggaattactc ggcacagaga tcgaaaccac    360
ggtcattact caaaccatga cttgggatgg cagaatctag aagaccaca cactaagatg    420 tcacatataa agggcatga aggagacccc tgcctacgat catcagactg cattgaaggg    480
ttttgctgtg ctcgtcattt ctggaccaaa atctgcaaac cagtgctcca tcaggggaa    540 gtctgtacca acaacgcaa gaagggttct catgggctgg aaattttcca gcgttgcgac    600
tgtgcgaagg gcctgtcttg caaagtatgg aaagatgcca cctactcctc caaagccaga    660
ctccatgtgt gtcagaaaat t                                             681

<210> SEQ ID NO 45
<211> LENGTH: 678
<212> TYPE: DNA
<213> ORGANISM: Artificial Sequence
<220> FEATURE:
<223> OTHER INFORMATION: Nucleic acid encoding DKK2 N-Gly3 polypeptide

<400> SEQUENCE: 45
aaactcaact ccatcaagtc ctctctgggc ggggagacgc ctggtcaggc cgccaatcga     60
tctgcgggca tgtaccaagg actggcattc ggcggcagta agaagggcaa aaacctgggg    120
caggcctacc cttgtagcag tgataaggag tgtgaagttg ggaggtattg ccacagtccc    180
caccaaggat catcggcctg catggtgtgt cggagaaaaa agaagcgctg ccaccgagat    240
ggcatgtgct gccccagtac ccgctgcaat aatggcatct gtatcaatgt tactgaaagc    300
atcttaaccc ctcacatccc ggctctggat ggtactcggc acagagatcg aaaccacggt    360
cattactcaa accatgactt gggatggcag aatctaggaa gaccacacac taagatgtca    420
catataaaag ggcatgaagg agacccctgc ctacgatcat cagactgcat tgaagggttt    480
tgctgtgctc gtcatttctg gaccaaaatc tgcaaaccag tgctccatca ggggaagtc    540 tgtaccaaac aacgcaagaa gggttctcat gggctggaaa ttttccagcg ttgcgactgt    600
gcgaagggcc tgtcttgcaa agtatggaaa gatgccacct actcctccaa agccagactc    660
catgtgtgtc agaaaatt                                                  678

<210> SEQ ID NO 46
<211> LENGTH: 678
<212> TYPE: DNA
<213> ORGANISM: Artificial Sequence
<220> FEATURE:

<223> OTHER INFORMATION: Nucleic acid encoding DKK2 N-Gly4 polypeptide

<400> SEQUENCE: 46

| | | |
|---|---|---|
| aaactcaact ccatcaagtc ctctctgggc ggggagacgc tggtcaggc cgccaatcga | 60 |
| tctgcgggca tgtaccaagg actggcattc ggcggcagta agaagggcaa aaacctgggg | 120 |
| caggcctacc cttgtagcag tgataaggag tgtgaagttg ggaggtattg ccacagtccc | 180 |
| caccaaggat catcggcctg catggtgtgt cggagaaaaa agaagcgctg ccaccgagat | 240 |
| ggcatgtgct gccccagtac ccgctgcaat aatggcatct gtatcccagt tactgaaagc | 300 |
| atcttaaccc ctcacatccc ggctctgaat ggtactcggc acagagatcg aaaccacggt | 360 |
| cattactcaa accatgactt gggatggcag atctaggaa gaccacacac taagatgtca | 420 |
| catataaaag gcatgaagg agaccccctgc ctacgatcat cagactgcat tgaagggttt | 480 |
| tgctgtgctc gtcatttctg gaccaaaatc tgcaaaccag tgctccatca ggggaagtc | 540 |
| tgtaccaaac aacgcaagaa gggttctcat gggctggaaa ttttccagcg ttgcgactgt | 600 |
| gcgaagggcc tgtcttgcaa agtatggaaa gatgccacct actcctccaa agccagactc | 660 |
| catgtgtgtc agaaaatt | 678 |

<210> SEQ ID NO 47
<211> LENGTH: 678
<212> TYPE: DNA
<213> ORGANISM: Artificial Sequence
<220> FEATURE:
<223> OTHER INFORMATION: Nucleic acid encoding DKK2 N-Gly5 polypeptide

<400> SEQUENCE: 47

| | | |
|---|---|---|
| aaactcaact ccatcaagtc ctctctgggc ggggagacgc tggtcaggc cgccaatcga | 60 |
| tctgcgggca tgtaccaagg actggcattc ggcggcagta agaagggcaa aaacctgggg | 120 |
| caggcctaca attgtagcag tgataaggag tgtgaagttg ggaggtattg ccacagtccc | 180 |
| caccaaggat catcggcctg catggtgtgt cggagaaaaa agaagcgctg ccaccgagat | 240 |
| ggcatgtgct gccccagtac ccgctgcaat aatggcatct gtatcccagt tactgaaagc | 300 |
| atcttaaccc ctcacatccc ggctctggat ggtactcggc acagagatcg aaaccacggt | 360 |
| cattactcaa accatgactt gggatggcag atctaggaa gaccacacac taagatgtca | 420 |
| catataaaag gcatgaagg agaccccctgc ctacgatcat cagactgcat tgaagggttt | 480 |
| tgctgtgctc gtcatttctg gaccaaaatc tgcaaaccag tgctccatca ggggaagtc | 540 |
| tgtaccaaac aacgcaagaa gggttctcat gggctggaaa ttttccagcg ttgcgactgt | 600 |
| gcgaagggcc tgtcttgcaa agtatggaaa gatgccacct actcctccaa agccagactc | 660 |
| catgtgtgtc agaaaatt | 678 |

<210> SEQ ID NO 48
<211> LENGTH: 696
<212> TYPE: DNA
<213> ORGANISM: Artificial Sequence
<220> FEATURE:
<223> OTHER INFORMATION: Nucleic acid encoding Fc region of human
    Immunoglobulin G1

<400> SEQUENCE: 48

| | | |
|---|---|---|
| gagcccaaat cttgtgacaa aactcacaca tgcccaccgt gcccagcacc tgaactcctg | 60 |
| ggggaccgt cagtcttcct cttccccca aaacccaagg acaccctcat gatctcccgg | 120 |
| acccctgagg tcacatgcgt ggtggtggac gtgagccacg aagaccctga ggtcaagttc | 180 |

```
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaa                              696
```

<210> SEQ ID NO 49
<211> LENGTH: 232
<212> TYPE: PRT
<213> ORGANISM: Artificial Sequence
<220> FEATURE:
<223> OTHER INFORMATION: Fc region of human Immunoglobulin G1

<400> SEQUENCE: 49

```
Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```